US 11,951,316 B2

(12) United States Patent
Oron et al.

(10) Patent No.: US 11,951,316 B2
(45) Date of Patent: Apr. 9, 2024

(54) ANTENNA CONFIGURATION

(71) Applicant: BLUEWIND MEDICAL LTD., Herzliya (IL)

(72) Inventors: Gur Oron, Tel Aviv (IL); Anton Plotkin, Tel Aviv (IL); Eran Benjamin, Tel Aviv (IL); Alexander Firtel, Ashdod (IL); Amiel Greenberg, Batya Mazkeret (IL); Yigal Elisha, Tel Aviv (IL)

(73) Assignee: BLUEWIND MEDICAL LTD., Herzliya (IL)

( * ) Notice: Subject to any disclaimer, the term of this patent is extended or adjusted under 35 U.S.C. 154(b) by 316 days.

(21) Appl. No.: 17/546,644

(22) Filed: Dec. 9, 2021

(65) Prior Publication Data

US 2022/0168580 A1 Jun. 2, 2022

Related U.S. Application Data

(60) Continuation of application No. 16/737,253, filed on Jan. 8, 2020, now Pat. No. 11,213,685, which is a
(Continued)

(51) Int. Cl.
*A61N 1/372* (2006.01)
*A61N 1/378* (2006.01)
(Continued)

(52) U.S. Cl.
CPC ....... *A61N 1/37229* (2013.01); *A61N 1/3787* (2013.01); *H02J 50/12* (2016.02);
(Continued)

(58) Field of Classification Search
CPC ... A61N 1/37229; A61N 1/3787; H02J 50/12; H02J 50/23; H02J 5/005; H02J 50/80; H04B 5/0056
(Continued)

(56) References Cited

U.S. PATENT DOCUMENTS 3,411,507 A 11/1968 Wingrove
3,693,625 A 9/1972 Auphan
(Continued)

FOREIGN PATENT DOCUMENTS

DE 102008054403 6/2010
EP 0 688 577 12/1995
(Continued)

OTHER PUBLICATIONS

Raab, Frederick. "Idealized operation of the class E tuned power amplifier." IEEE transactions on Circuits and Systems 24.12 (1977): 725-735.
(Continued)

*Primary Examiner* — Erin M Piateski
(74) *Attorney, Agent, or Firm* — Sughrue Mion, PLLC

(57) ABSTRACT

Apparatus for use with a medical implant having a receiving coil. A flexible housing to be placed against skin of a subject includes a flexible transmitting coil and control circuitry for driving a current through the transmitting coil to induce a current in the receiving coil. A sensor coupled to the circuitry determines divergence of a resonance frequency of the transmitting coil when flexed from a nominal resonance frequency of the transmitting coil, occurring in the absence of any forces applied to the transmitting coil. One or more electrical components coupled to the circuitry tune the resonance frequency of the transmitting coil. A switch is coupled to each of the electrical components, the switches including transistors having capacitances that depend on the voltage applied to each switch. The circuitry applies a respective DC voltage to each switch. Other applications are also described.

10 Claims, 13 Drawing Sheets

Related U.S. Application Data division of application No. 15/621,433, filed on Jun. 13, 2017, now abandoned.

(51) Int. Cl.
*H02J 5/00* (2016.01)
*H02J 50/12* (2016.01)
*H02J 50/23* (2016.01)
*H02J 50/80* (2016.01)
*H04B 5/00* (2006.01)

(52) U.S. Cl.
CPC ............ *H02J 50/23* (2016.02); *H04B 5/0056* (2013.01); *H02J 50/80* (2016.02)

(58) Field of Classification Search
USPC .......................................................... 607/61
See application file for complete search history.

(56) References Cited

U.S. PATENT DOCUMENTS

| | | |
|---|---|---|
| 3,727,616 A | 4/1973 | Lenzkes |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lau |
| 4,741,339 A | 5/1988 | Harrison et al. |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,036,854 A | 8/1991 | Schollmeyer et al. |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,453 A | 5/1994 | Jeutter |
| 5,314,495 A | 5/1994 | Kovacs |
| 5,330,507 A | 7/1994 | Schwartz |
| 5,335,657 A | 8/1994 | Terry, Jr. |
| 5,411,535 A | 5/1995 | Fujii et al. |
| 5,423,872 A | 6/1995 | Cigaina |
| 5,439,938 A | 8/1995 | Synder et al. |
| 5,454,840 A | 10/1995 | Krakovsky et al. |
| 5,487,760 A | 1/1996 | Villafana |
| 5,505,201 A | 4/1996 | Grill, Jr. |
| 5,509,924 A | 4/1996 | Paspa et al. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,898,579 A | 4/1999 | Boys et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,070,803 A | 6/2000 | Stobbe |
| 6,071,274 A | 6/2000 | Thompson et al. |
| 6,083,249 A | 7/2000 | Familoni |
| 6,086,525 A | 7/2000 | Davey et al. |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Schwartz |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,496,729 B2 | 12/2002 | Thompson |
| 6,496,730 B1 | 12/2002 | Kleckner et al. |
| 6,582,441 B1 | 6/2003 | He et al. |
| 6,591,139 B2 | 7/2003 | Loftin et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,712,772 B2 | 3/2004 | Cohen et al. |
| 6,721,603 B2 | 4/2004 | Zabara et al. |
| 6,735,474 B1 | 5/2004 | Loeb et al. |
| 6,735,475 B1 | 5/2004 | Whitehurst et al. |

(56) References Cited

U.S. PATENT DOCUMENTS

| | | |
|---|---|---|
| 6,770,022 B2 | 8/2004 | Mechlenburg |
| 6,788,973 B2 | 9/2004 | Davis et al. |
| 6,788,975 B1 | 9/2004 | Whitehurst et al. |
| 6,804,561 B2 | 10/2004 | Stover |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 6,950,706 B2 | 9/2005 | Rodriguez et al. |
| 6,993,384 B2 | 1/2006 | Bradley et al. |
| 7,015,769 B2 | 3/2006 | Schulman et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,689 B1 | 5/2006 | Whitehurst et al. |
| 7,054,692 B1 | 5/2006 | Whitehurst et al. |
| 7,110,820 B2 | 9/2006 | Tcheng et al. |
| 7,149,575 B2 | 12/2006 | Ostroff et al. |
| 7,151,914 B2 | 12/2006 | Brewer |
| 7,174,218 B1 | 2/2007 | Kuzma |
| 7,177,690 B2 | 2/2007 | Woods et al. |
| 7,177,698 B2 | 2/2007 | Klosterman et al. |
| 7,190,153 B2 | 3/2007 | Stover et al. |
| 7,190,998 B2 | 3/2007 | Shalev et al. |
| 7,203,549 B2 | 4/2007 | Schommer et al. |
| 7,209,792 B1 | 4/2007 | Parramon et al. |
| 7,212,867 B2 | 5/2007 | Venrooij et al. |
| 7,216,000 B2 | 5/2007 | Sieracki et al. |
| 7,225,032 B2 | 5/2007 | Schmeling et al. |
| 7,228,178 B2 | 6/2007 | Carroll |
| 7,239,921 B2 | 7/2007 | Canfield et al. |
| 7,242,982 B2 | 7/2007 | Singhal et al. |
| 7,254,449 B2 | 8/2007 | Karunasiri |
| 7,263,402 B2 | 8/2007 | Thacker et al. |
| 7,277,748 B2 | 10/2007 | Wingeier et al. |
| 7,277,749 B2 | 10/2007 | Gordon et al. |
| 7,286,880 B2 | 10/2007 | Olson et al. |
| 7,286,881 B2 | 10/2007 | Schommer et al. |
| 7,289,853 B1 | 10/2007 | Campbell et al. |
| 7,292,890 B2 | 11/2007 | Whitehurst et al. |
| 7,308,316 B2 | 12/2007 | Schommer |
| 7,324,852 B2 | 1/2008 | Barolat et al. |
| 7,324,853 B2 | 1/2008 | Ayal |
| 7,330,756 B2 | 2/2008 | Marnfeldt |
| 7,337,007 B2 | 2/2008 | Nathan et al. |
| 7,342,508 B2 | 3/2008 | Morgan et al. |
| 7,363,087 B2 | 4/2008 | Nghiem et al. |
| 7,376,466 B2 | 5/2008 | He et al. |
| 7,389,145 B2 | 6/2008 | Kilgore et al. |
| 7,483,748 B2 | 1/2009 | Torgerson et al. |
| 7,483,752 B2 | 1/2009 | Von arx et al. |
| 7,489,561 B2 | 2/2009 | Armstrong et al. |
| 7,502,652 B2 | 3/2009 | Gaunt et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,536,226 B2 | 5/2009 | Williams |
| 7,539,538 B2 | 5/2009 | Parramon et al. |
| 7,561,921 B2 | 7/2009 | Phillips et al. |
| 7,565,204 B2 | 7/2009 | Matei |
| 7,628,750 B2 | 12/2009 | Cohen |
| 7,630,771 B2 | 12/2009 | Cauller |
| 7,634,313 B1 | 12/2009 | Kroll et al. |
| 7,643,147 B2 | 1/2010 | Pless |
| 7,647,117 B2 | 1/2010 | Bauhahn |
| 7,650,192 B2 | 1/2010 | Wahlstrand |
| 7,655,014 B2 | 2/2010 | Ko et al. |
| 7,657,311 B2 | 2/2010 | Bardy et al. |
| 7,657,317 B2 | 2/2010 | Thacker et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,680,540 B2 | 3/2010 | Jensen et al. |
| 7,711,434 B2 | 5/2010 | Denker et al. |
| 7,736,379 B2 | 6/2010 | Ewers et al. |
| 7,747,325 B2 | 6/2010 | Dilorenzo |
| 7,748,344 B2 | 7/2010 | Divergilio et al. |
| 7,780,625 B2 | 8/2010 | Bardy |
| 7,797,050 B2 | 9/2010 | Libbus et al. |
| 7,801,602 B2 | 9/2010 | McClure et al. |
| 7,803,142 B2 | 9/2010 | Longson et al. |
| 7,809,437 B2 | 10/2010 | Palmer et al. |
| 7,817,280 B2 | 10/2010 | Pless |
| 7,822,480 B2 | 10/2010 | Park et al. |
| 7,848,818 B2 | 12/2010 | Barolat et al. |
| 7,869,867 B2 | 1/2011 | Armstrong et al. |
| 7,894,905 B2 | 2/2011 | Pless et al. |
| 7,899,547 B1 | 3/2011 | Emadi et al. |
| 7,899,556 B2 | 3/2011 | Nathan et al. |
| 7,904,171 B2 | 3/2011 | Parramon et al. |
| 7,912,551 B2 | 3/2011 | Wosmek |
| 7,925,350 B1 | 4/2011 | Palmer |
| 7,917,226 B2 | 5/2011 | Nghiem |
| 7,937,148 B2 | 5/2011 | Jacobson |
| 7,941,218 B2 | 5/2011 | Sambelashvili et al. |
| 7,962,211 B2 | 6/2011 | Torgerson et al. |
| 7,962,220 B2 | 6/2011 | Kolafa et al. |
| 7,974,706 B2 | 7/2011 | Moffitt et al. |
| 7,979,126 B2 | 7/2011 | Payne et al. |
| 7,991,467 B2 | 8/2011 | Markowitz et al. |
| 7,996,079 B2 | 8/2011 | Armstrong |
| 7,996,089 B2 | 8/2011 | Haugland et al. |
| 7,996,092 B2 | 8/2011 | Mrva et al. |
| 8,005,547 B2 | 8/2011 | Forsberg et al. |
| 8,019,443 B2 | 9/2011 | Scheicher et al. |
| 8,050,771 B2 | 11/2011 | Yamamoto et al. |
| 8,055,336 B1 | 11/2011 | Schulman et al. |
| 8,055,350 B2 | 11/2011 | Roberts |
| 8,075,556 B2 | 12/2011 | Betts |
| 8,086,313 B2 | 12/2011 | Singhal et al. |
| 8,090,438 B2 | 1/2012 | Bardy et al. |
| 8,092,412 B2 | 1/2012 | Sherman |
| 8,115,448 B2 | 2/2012 | John |
| 8,127,424 B2 | 3/2012 | Haller et al. |
| 8,131,377 B2 | 3/2012 | Shhi et al. |
| 8,140,168 B2 | 3/2012 | Olson et al. |
| 8,170,675 B2 | 5/2012 | Alataris et al. |
| 8,170,681 B2 | 5/2012 | Jimenez et al. |
| 8,175,719 B2 | 5/2012 | Shi et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,219,205 B2 | 7/2012 | Tseng et al. |
| 8,224,453 B2 | 7/2012 | De Ridder |
| 8,229,567 B2 | 7/2012 | Phillips et al. |
| 8,244,367 B2 | 8/2012 | Wahlstrand et al. |
| 8,255,057 B2 | 8/2012 | Fang et al. |
| 8,260,432 B2 | 9/2012 | DiGiore et al. |
| 8,265,770 B2 | 9/2012 | Toy et al. |
| 8,306,627 B2 | 11/2012 | Armstrong |
| 8,311,638 B2 | 11/2012 | Aghassian |
| 8,321,028 B1 | 11/2012 | Thenuwara et al. |
| 8,335,569 B2 | 12/2012 | Aghassian |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,267 B2 | 1/2013 | Schleicher et al. |
| 8,369,963 B2 | 2/2013 | Parramon et al. |
| 8,374,700 B2 | 2/2013 | Haubrich et al. |
| 8,386,047 B2 | 2/2013 | Koester |
| 8,386,048 B2 | 2/2013 | McClure et al. |
| 8,396,559 B2 | 3/2013 | Alataris et al. |
| 8,428,731 B2 | 4/2013 | Armstrong |
| 8,428,744 B2 | 4/2013 | Stancer et al. |
| 8,428,746 B2 | 4/2013 | DiGiore et al. |
| 8,428,748 B2 | 4/2013 | Alataris et al. |
| 8,437,846 B2 | 5/2013 | Swoyer et al. |
| 8,437,853 B2 | 5/2013 | Inman et al. |
| 8,457,744 B2 | 6/2013 | Janzig et al. |
| 8,457,759 B2 | 6/2013 | Parker et al. |
| 8,463,404 B2 | 6/2013 | Levi et al. |
| 8,473,066 B2 | 6/2013 | Aghassian et al. |
| 8,478,420 B2 | 7/2013 | Armstrong et al. |

(56) References Cited

U.S. PATENT DOCUMENTS

| | | |
|---|---|---|
| 8,483,838 B2 | 7/2013 | Nghiem et al. |
| 8,483,845 B2 | 7/2013 | Sage |
| 8,494,640 B2 | 7/2013 | Peterson et al. |
| 8,494,650 B2 | 7/2013 | Glukhovsky et al. |
| 8,497,804 B2 | 7/2013 | Haubrich et al. |
| 8,498,716 B2 | 7/2013 | Chen et al. |
| 8,509,905 B2 | 8/2013 | Alataris et al. |
| 8,509,906 B2 | 8/2013 | Walker et al. |
| 8,515,558 B1 | 8/2013 | Zweber et al. |
| 8,538,548 B2 | 9/2013 | Shi et al. |
| 8,543,200 B2 | 9/2013 | Lane et al. |
| 8,554,326 B2 | 10/2013 | Alataris et al. |
| 8,555,894 B2 | 10/2013 | Schulman et al. |
| 8,571,651 B2 | 10/2013 | Ben-ezra et al. |
| 8,577,474 B2 | 11/2013 | Rahman et al. |
| 8,588,933 B2 | 11/2013 | Floyd et al. |
| 8,612,014 B2 | 12/2013 | Rahman et al. |
| 8,612,019 B2 | 12/2013 | Moffitt |
| 8,620,435 B2 | 12/2013 | Rooney et al. |
| 8,620,449 B2 | 12/2013 | Zhao et al. |
| 8,626,310 B2 | 1/2014 | Barror et al. |
| 8,634,927 B2 | 1/2014 | Olson et al. |
| 8,644,947 B2 | 2/2014 | Zhu et al. |
| 8,644,948 B2 | 2/2014 | Grevious et al. |
| 8,649,874 B2 | 2/2014 | Alataris et al. |
| 8,660,655 B2 | 2/2014 | Peterson et al. |
| 8,665,086 B2 | 3/2014 | Miller et al. |
| 8,666,491 B2 | 3/2014 | Chen et al. |
| 8,666,504 B2 | 3/2014 | Dronov et al. |
| 8,676,337 B2 | 3/2014 | Kallmyer |
| 8,676,341 B2 | 3/2014 | Kane et al. |
| 8,688,232 B2 | 4/2014 | Finley et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,712,534 B2 | 4/2014 | Wei |
| 8,718,780 B2 | 5/2014 | Lee |
| 8,718,781 B2 | 5/2014 | Alataris et al. |
| 8,718,782 B2 | 5/2014 | Alataris et al. |
| 8,738,145 B2 | 5/2014 | Goetz et al. |
| 8,750,985 B2 | 6/2014 | Parramon et al. |
| 8,751,009 B2 | 6/2014 | Wacnik |
| 8,755,893 B2 | 6/2014 | Gross et al. |
| 8,761,895 B2 | 6/2014 | Stevenson et al. |
| 8,768,472 B2 | 7/2014 | Fang et al. |
| 8,774,912 B2 | 7/2014 | Gerber |
| 8,774,926 B2 | 7/2014 | Alataris et al. |
| 8,788,045 B2 | 7/2014 | Gross et al. |
| 8,792,988 B2 | 7/2014 | Alataris et al. |
| 8,798,773 B2 | 8/2014 | Mashiach |
| 8,805,519 B2 | 8/2014 | Parker et al. |
| 8,812,135 B2 | 8/2014 | Mashiach |
| 8,831,730 B2 | 9/2014 | Mashiach et al. |
| 8,843,203 B2 | 9/2014 | Lee et al. |
| 8,849,410 B2 | 9/2014 | Walker et al. |
| 8,849,412 B2 | 9/2014 | Perryman et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,219 B2 | 10/2014 | Trier et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,884,779 B2 | 11/2014 | Herman et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,892,214 B2 | 11/2014 | Bonde et al. |
| 8,903,497 B2 | 12/2014 | Norgaard et al. |
| 8,903,499 B2 | 12/2014 | Pless et al. |
| 8,903,515 B2 | 12/2014 | Mashiach |
| 8,918,179 B2 | 12/2014 | Peterson et al. |
| 8,918,180 B2 | 12/2014 | Peterson |
| 8,923,988 B2 | 12/2014 | Bradley |
| 8,942,808 B2 | 1/2015 | Peterson et al. |
| 8,948,871 B2 | 2/2015 | Mashiach et al. |
| 8,954,165 B2 | 2/2015 | Sharma et al. |
| 8,958,884 B2 | 2/2015 | Kothandaraman et al. |
| 8,958,891 B2 | 2/2015 | Kane et al. |
| 8,983,615 B2 | 3/2015 | Tahmasian et al. |
| 8,983,618 B2 | 3/2015 | Yamamoto et al. |
| 8,989,864 B2 | 3/2015 | Funderburk et al. |
| 8,989,868 B2 | 3/2015 | Mashiach et al. |
| 8,994,325 B2 | 3/2015 | Carbunaru et al. |
| 8,996,115 B2 | 3/2015 | Trier et al. |
| 9,002,445 B2 | 4/2015 | Chen |
| 9,002,460 B2 | 4/2015 | Parker |
| 9,002,461 B2 | 4/2015 | Walker et al. |
| 9,002,466 B2 | 4/2015 | Trier et al. |
| 9,020,599 B2 | 4/2015 | Rooney et al. |
| 9,020,602 B2 | 4/2015 | Aghassian |
| 9,026,227 B2 | 5/2015 | Daglow |
| 9,030,159 B2 | 5/2015 | Chen et al. |
| 9,031,653 B2 | 5/2015 | Mashiach |
| 9,031,666 B2 | 5/2015 | Fell |
| 9,037,261 B2 | 5/2015 | Bradley |
| 9,042,997 B2 | 5/2015 | Rahman et al. |
| 9,044,616 B2 | 6/2015 | Chen et al. |
| 9,056,206 B2 | 6/2015 | Torgerson et al. |
| 9,061,140 B2 | 6/2015 | Shi et al. |
| 9,061,151 B2 | 6/2015 | Mashiach et al. |
| 9,061,159 B2 | 6/2015 | Rahman |
| 9,061,162 B2 | 6/2015 | Mashiach et al. |
| 9,067,072 B2 | 6/2015 | Tahmasian et al. |
| 9,070,507 B2 | 6/2015 | Dronov et al. |
| 9,072,896 B2 | 7/2015 | Dar et al. |
| 9,079,041 B2 | 7/2015 | Park et al. |
| 9,084,900 B2 | 7/2015 | Hershey et al. |
| 9,089,712 B2 | 7/2015 | Joshi et al. |
| 9,095,725 B2 | 8/2015 | Mashiach |
| 9,095,726 B2 | 8/2015 | Parramon et al. |
| 9,101,774 B2 | 8/2015 | Mashiach et al. |
| 9,119,969 B2 | 9/2015 | Vansickle |
| 9,142,989 B2 | 9/2015 | Fell et al. |
| 9,149,635 B2 | 10/2015 | Denison et al. |
| 9,149,643 B2 | 10/2015 | Tahmasian et al. |
| 9,154,219 B2 | 10/2015 | Polefko et al. |
| 9,155,899 B2 | 10/2015 | Mashiach et al. |
| 9,155,901 B2 | 10/2015 | Dearden et al. |
| 9,162,068 B2 | 10/2015 | Dronov |
| 9,174,051 B2 | 11/2015 | Marnfeldt et al. |
| 9,174,053 B2 | 11/2015 | Zhu |
| 9,186,504 B2 | 11/2015 | Gross |
| 9,192,770 B2 | 11/2015 | Wang et al. |
| 9,199,083 B2 | 12/2015 | Caparso et al. |
| 9,205,258 B2 | 12/2015 | Simon et al. |
| 9,211,418 B2 | 12/2015 | Aghassian |
| 9,216,297 B2 | 12/2015 | Kast et al. |
| 9,220,907 B2 | 12/2015 | Mashiach et al. |
| 9,220,908 B2 | 12/2015 | Mashiach |
| 9,220,909 B2 | 12/2015 | Carbunaru et al. |
| 9,220,910 B2 | 12/2015 | Colborn |
| 9,225,194 B2 | 12/2015 | Joshi |
| D747,491 S | 1/2016 | Thompson et al. |
| 9,227,075 B2 | 1/2016 | Aghassian et al. |
| 9,232,903 B2 | 1/2016 | Pless et al. |
| 9,238,138 B2 | 1/2016 | Lee et al. |
| 9,240,630 B2 | 1/2016 | Joshi |
| 9,242,106 B2 | 1/2016 | Klosterman et al. |
| 9,248,279 B2 | 2/2016 | Chen et al. |
| 9,248,292 B2 | 2/2016 | Trier et al. |
| 9,248,302 B2 | 2/2016 | Mashiach et al. |
| 9,252,604 B2 | 2/2016 | Kim |
| 9,254,393 B2 | 2/2016 | Perryman et al. |
| 9,259,571 B2 | 2/2016 | Straka et al. |
| 9,259,582 B2 | 2/2016 | Joshi et al. |
| 9,259,584 B2 | 2/2016 | Bauhahn et al. |
| 9,265,941 B2 | 2/2016 | Van Den Biggelaar et al. |
| 9,265,958 B2 | 2/2016 | Joshi et al. |
| 9,289,616 B2 | 3/2016 | Koester |
| 9,295,841 B2 | 3/2016 | Fang et al. |
| 9,295,850 B2 | 3/2016 | Kallmyer |
| 9,314,613 B2 | 4/2016 | Mashiach |

(56) References Cited

U.S. PATENT DOCUMENTS

| | | |
|---|---|---|
| 9,314,628 B2 | 4/2016 | North et al. |
| 9,314,642 B2 | 4/2016 | Ozawa et al. |
| 9,320,847 B2 | 4/2016 | Rooney et al. |
| 9,320,899 B2 | 4/2016 | Parramon et al. |
| 9,320,908 B2 | 4/2016 | Fletcher et al. |
| 9,327,132 B2 | 5/2016 | Mashiach |
| 9,333,367 B2 | 5/2016 | Chen |
| 9,339,660 B2 | 5/2016 | Feldman et al. |
| 9,343,923 B2 | 5/2016 | Joshi |
| 9,352,161 B2 | 5/2016 | Thacker et al. |
| 9,370,664 B2 | 6/2016 | Marnfeldt et al. |
| 9,375,582 B2 | 6/2016 | Kaula et al. |
| 9,381,360 B2 | 7/2016 | Hershey |
| 9,387,331 B2 | 7/2016 | Zhao et al. |
| 9,387,332 B2 | 7/2016 | Zhao et al. |
| 9,393,423 B2 | 7/2016 | Parramon et al. |
| 9,393,428 B2 | 7/2016 | Nyberg, II et al. |
| 9,393,435 B2 | 7/2016 | Mashiach |
| 9,398,901 B2 | 7/2016 | Tischendorf et al. |
| 9,399,130 B2 | 7/2016 | Bonde et al. |
| 9,399,131 B2 | 7/2016 | Digiore et al. |
| 9,399,143 B2 | 7/2016 | Yamamoto et al. |
| 9,403,013 B2 | 8/2016 | Walker et al. |
| 9,403,020 B2 | 8/2016 | Wingeier |
| 9,403,021 B2 | 8/2016 | Dronov |
| 9,407,110 B2 | 8/2016 | Lui et al. |
| 9,409,029 B2 | 8/2016 | Perryman et al. |
| 9,435,830 B2 | 9/2016 | Joshi |
| 9,446,251 B1 | 9/2016 | Perryman et al. |
| 9,446,254 B2 | 9/2016 | Ozawa et al. |
| 9,449,501 B2 | 9/2016 | Grevious et al. |
| 9,452,288 B2 | 9/2016 | Whitehurst et al. |
| 9,457,186 B2 | 10/2016 | Gross |
| 9,463,321 B2 | 10/2016 | Bradley et al. |
| 9,463,323 B2 | 10/2016 | Lee et al. |
| 9,463,326 B2 | 10/2016 | Ranu |
| 9,468,771 B2 | 10/2016 | Griffith et al. |
| 9,468,772 B2 | 10/2016 | Demmer |
| 9,469,437 B2 | 10/2016 | Kamath |
| 9,474,905 B2 | 10/2016 | Doan et al. |
| 9,480,841 B2 | 11/2016 | Hershey et al. |
| 9,504,832 B2 | 11/2016 | Libbus et al. |
| 9,504,838 B2 | 11/2016 | Rao et al. |
| 9,511,238 B2 | 12/2016 | Mashiach |
| 9,517,344 B1 | 12/2016 | Bradley |
| 9,517,352 B2 | 12/2016 | Kast et al. |
| 9,522,270 B2 | 12/2016 | Perryman et al. |
| 9,526,906 B2 | 12/2016 | Mashiach |
| 9,533,148 B2 | 1/2017 | Carcieri |
| 9,533,153 B2 | 1/2017 | Libbus et al. |
| 9,533,154 B2 | 1/2017 | Kothandaraman et al. |
| 9,533,162 B2 | 1/2017 | Ter-petrosyan et al. |
| 9,555,257 B2 | 1/2017 | Mashiach et al. |
| 9,561,365 B2 | 2/2017 | Shi et al. |
| 9,585,642 B2 | 3/2017 | Dinsmoor et al. |
| 9,586,054 B2 | 3/2017 | Aghassian |
| 9,592,385 B2 | 3/2017 | Kaula et al. |
| 9,597,516 B2 | 3/2017 | Lee et al. |
| 9,597,517 B2 | 3/2017 | Moffitt |
| 9,597,521 B2 | 3/2017 | Plotkin et al. |
| 9,610,450 B2 | 4/2017 | Zhao |
| 9,616,230 B2 | 4/2017 | Grandhe |
| 9,623,244 B2 | 4/2017 | Kothandaraman |
| 9,623,245 B2 | 4/2017 | King et al. |
| 9,623,253 B2 | 4/2017 | Perryman et al. |
| 9,623,257 B2 | 4/2017 | Olson et al. |
| 9,630,231 B2 | 4/2017 | Kelsch et al. |
| 9,636,508 B2 | 5/2017 | Chen et al. |
| 9,643,022 B2 | 5/2017 | Mashiach et al. |
| 9,649,049 B2 | 5/2017 | Pless et al. |
| 9,649,493 B2 | 5/2017 | Mashiach |
| 9,653,941 B2 | 5/2017 | Dinsmoor et al. |
| 9,656,074 B2 | 5/2017 | Simon et al. |
| 9,656,076 B2 | 5/2017 | Trier et al. |
| 9,656,081 B2 | 5/2017 | Feldman et al. |
| 9,675,809 B2 | 6/2017 | Chow |
| 9,687,649 B2 | 6/2017 | Thacker |
| 9,700,725 B2 | 7/2017 | Zhu |
| 9,700,730 B2 | 7/2017 | Carbunaru et al. |
| 9,707,404 B2 | 7/2017 | Rao et al. |
| 9,713,707 B2 | 7/2017 | Oron et al. |
| 9,713,717 B2 | 7/2017 | Aghassian |
| 9,713,718 B2 | 7/2017 | Lamont et al. |
| 9,713,721 B2 | 7/2017 | Kothandaraman |
| 9,724,513 B2 | 8/2017 | Lane et al. |
| 9,731,116 B2 | 8/2017 | Chen |
| 9,737,703 B2 | 8/2017 | Carbunaru et al. |
| 9,737,714 B2 | 8/2017 | Zottola |
| 9,744,347 B2 | 8/2017 | Chen et al. |
| 9,744,362 B2 | 8/2017 | Steinke et al. |
| 9,744,365 B2 | 8/2017 | Davis et al. |
| 9,744,368 B2 | 8/2017 | Dinsmoor |
| 9,750,930 B2 | 9/2017 | Chen |
| 9,782,588 B2 | 10/2017 | Shi et al. |
| 9,782,593 B2 | 10/2017 | Parramon et al. |
| 9,782,596 B2 | 10/2017 | Vamos et al. |
| 9,789,314 B2 | 10/2017 | Perryman et al. |
| 9,789,321 B2 | 10/2017 | Dixit et al. |
| 9,789,324 B2 | 10/2017 | Bauhahn et al. |
| 9,802,038 B2 | 10/2017 | Lee et al. |
| 9,802,048 B2 | 10/2017 | Armstrong |
| 9,802,052 B2 | 10/2017 | Marnfeldt |
| 9,814,458 B2 | 11/2017 | North |
| 9,814,880 B2 | 11/2017 | Hershey et al. |
| 9,814,884 B2 | 11/2017 | Parker et al. |
| 9,839,786 B2 | 12/2017 | Rondoni et al. |
| 9,844,677 B2 | 12/2017 | Aghassian |
| 9,849,298 B2 | 12/2017 | Ozawa et al. |
| 9,855,032 B2 | 1/2018 | Mashiach et al. |
| 9,855,436 B2 | 1/2018 | Dearden et al. |
| 9,861,825 B2 | 1/2018 | Ozawa et al. |
| 9,867,989 B2 | 1/2018 | Blum et al. |
| 9,867,994 B2 | 1/2018 | Parramon |
| 9,878,158 B2 | 1/2018 | Hershey et al. |
| 9,907,967 B2 | 3/2018 | Mashiach et al. |
| 9,913,980 B2 | 3/2018 | Ostroff et al. |
| 9,913,983 B2 | 3/2018 | Gustafsson et al. |
| 9,913,986 B2 | 3/2018 | Chow et al. |
| 9,913,990 B2 | 3/2018 | Ter-petrosyan et al. |
| 9,925,381 B2 | 3/2018 | Nassif |
| 9,929,584 B2 | 3/2018 | Aghassian et al. |
| 9,931,107 B2 | 4/2018 | Tischendorf et al. |
| 9,935,498 B2 | 4/2018 | Joshi |
| 9,943,685 B2 | 4/2018 | Ramesh et al. |
| 9,950,166 B2 | 4/2018 | Mashiach et al. |
| 9,950,173 B2 | 4/2018 | Doan |
| 9,950,179 B2 | 4/2018 | Bonde et al. |
| 9,956,419 B2 | 5/2018 | Bokil |
| 9,956,421 B2 | 5/2018 | Bunyan et al. |
| 9,974,965 B2 | 5/2018 | Perryman et al. |
| 9,981,130 B2 | 5/2018 | Lee |
| 9,993,645 B2 | 6/2018 | Walker et al. |
| 10,010,717 B2 | 7/2018 | Aghassian et al. |
| 10,014,571 B2 | 7/2018 | Andersen et al. |
| 10,052,097 B2 | 8/2018 | Mashiach et al. |
| 10,056,688 B2 | 8/2018 | Andersen et al. |
| 10,058,705 B2 | 8/2018 | Andersen et al. |
| 10,064,288 B2 | 8/2018 | Li et al. |
| 10,080,902 B2 | 9/2018 | Dinsmoor et al. |
| 10,105,540 B2 | 10/2018 | Oron et al. |
| 10,105,542 B2 | 10/2018 | Jiang et al. |
| 10,105,543 B2 | 10/2018 | Marnfeldt et al. |
| 10,118,040 B2 | 11/2018 | Zhu |
| 10,143,845 B2 | 12/2018 | Kothandaraman |
| 10,149,976 B1 | 12/2018 | Andresen et al. |
| 10,173,062 B2 | 1/2019 | Parker |
| 10,177,609 B2 | 1/2019 | Olson et al. |
| 10,179,241 B2 | 1/2019 | Walker et al. |
| 10,182,807 B2 | 1/2019 | Bridgeman et al. |
| 10,195,425 B2 | 2/2019 | Ostroff et al. |
| 10,213,608 B2 | 2/2019 | Moffitt |
| 10,219,229 B1 | 2/2019 | Mulligan, IV |
| 10,226,637 B2 | 3/2019 | Aghassian et al. |
| 10,532,208 B2 | 1/2020 | Ostroff et al. |

(56) References Cited

U.S. PATENT DOCUMENTS

| | | | |
|---|---|---|---|
| 10,583,284 B2 | 3/2020 | Peters et al. | |
| 11,083,903 B2 | 8/2021 | Nassif et al. | |
| 2002/0077554 A1 | 6/2002 | Schwartz et al. | |
| 2002/0099419 A1 | 7/2002 | Cohen et al. | |
| 2002/0124848 A1 | 9/2002 | Sullivan et al. | |
| 2002/0183805 A1 | 12/2002 | Fang et al. | |
| 2002/0183817 A1 | 12/2002 | Van Venrooij et al. | |
| 2003/0014016 A1 | 1/2003 | Purdy | |
| 2003/0040774 A1 | 2/2003 | Terry et al. | |
| 2003/0060858 A1 | 3/2003 | Kieval et al. | |
| 2003/0100933 A1 | 5/2003 | Ayal | |
| 2003/0176898 A1 | 9/2003 | Gross et al. | |
| 2003/0236557 A1 | 12/2003 | Whitehurst et al. | |
| 2003/0236558 A1 | 12/2003 | Whitehurst et al. | |
| 2004/0015205 A1 | 1/2004 | Whitehurst et al. | |
| 2004/0019368 A1 | 1/2004 | Lattner et al. | |
| 2004/0048795 A1 | 3/2004 | Ivanova et al. | |
| 2004/0073270 A1 | 4/2004 | Firlik et al. | |
| 2004/0254624 A1 | 6/2004 | Johnson | |
| 2004/0167584 A1 | 8/2004 | Carroll et al. | |
| 2004/0249431 A1 | 12/2004 | Ransbury et al. | |
| 2004/0254612 A1 | 12/2004 | Ezra et al. | |
| 2005/0119716 A1* | 6/2005 | McClure | A61N 1/37276 607/61 |
| 2005/0131495 A1 | 6/2005 | Parramon et al. | |
| 2005/0143789 A1 | 6/2005 | Whitehurst | |
| 2005/0165457 A1 | 7/2005 | Benser et al. | |
| 2005/0182457 A1 | 8/2005 | Thrope et al. | |
| 2005/0251061 A1 | 11/2005 | Schuler et al. | |
| 2006/0020305 A1 | 1/2006 | Desai et al. | |
| 2006/0047327 A1 | 3/2006 | Colvin et al. | |
| 2006/0085039 A1 | 4/2006 | Hastings et al. | |
| 2006/0100668 A1 | 5/2006 | Ben-David et al. | |
| 2006/0155345 A1 | 7/2006 | Williams et al. | |
| 2006/0271137 A1 | 11/2006 | Stanton-Hicks | |
| 2007/0032827 A1 | 2/2007 | Katims | |
| 2007/0067000 A1 | 3/2007 | Strother et al. | |
| 2007/0067007 A1 | 3/2007 | Schulman | |
| 2007/0073353 A1 | 3/2007 | Rooney et al. | |
| 2007/0073354 A1 | 3/2007 | Knudson et al. | |
| 2007/0083240 A1 | 4/2007 | Peterson et al. | |
| 2007/0088397 A1 | 4/2007 | Jacobson | |
| 2007/0173893 A1 | 7/2007 | Pitts | |
| 2007/0208392 A1 | 9/2007 | Kuschner et al. | |
| 2007/0255349 A1 | 11/2007 | Torgerson et al. | |
| 2007/0293908 A1 | 12/2007 | Cowan et al. | |
| 2007/0293912 A1 | 12/2007 | Cowan et al. | |
| 2008/0004535 A1 | 1/2008 | Smits | |
| 2008/0009914 A1 | 1/2008 | Buysman et al. | |
| 2008/0021336 A1 | 1/2008 | Dobak | |
| 2008/0027513 A1 | 1/2008 | Carbunaru | |
| 2008/0039915 A1 | 2/2008 | Van Den Biggelaar | |
| 2008/0065182 A1 | 3/2008 | Strother et al. | |
| 2008/0071178 A1 | 3/2008 | Greenland et al. | |
| 2008/0091255 A1 | 4/2008 | Caparso et al. | |
| 2008/0103407 A1 | 5/2008 | Bolea et al. | |
| 2008/0103572 A1 | 5/2008 | Gerber | |
| 2008/0109054 A1 | 5/2008 | Hastings et al. | |
| 2008/0119911 A1 | 5/2008 | Rosero | |
| 2008/0132964 A1 | 6/2008 | Cohen et al. | |
| 2008/0183235 A1 | 7/2008 | Stancer et al. | |
| 2008/0269740 A1 | 10/2008 | Bonde et al. | |
| 2009/0012590 A1 | 1/2009 | Inman et al. | |
| 2009/0036975 A1 | 2/2009 | Ward et al. | |
| 2009/0048642 A1 | 2/2009 | Goroszeniuk | |
| 2009/0149912 A1 | 6/2009 | Dacey et al. | |
| 2009/0152954 A1 | 6/2009 | Le et al. | |
| 2009/0182402 A1 | 7/2009 | Glukhovsky | |
| 2009/0204170 A1 | 8/2009 | Hastings et al. | |
| 2009/0204173 A1 | 8/2009 | Fang et al. | |
| 2009/0234407 A1 | 9/2009 | Hastings et al. | |
| 2009/0259280 A1 | 10/2009 | Wilkin et al. | |
| 2009/0270951 A1 | 10/2009 | Kallmyer | |
| 2009/0281594 A1 | 11/2009 | King et al. | |
| 2009/0326602 A1 | 12/2009 | Glukhovsky et al. | |
| 2010/0069992 A1 | 3/2010 | Aghassian et al. | |
| 2010/0094367 A1 | 4/2010 | Sen | |
| 2010/0121405 A1 | 5/2010 | Ternes et al. | |
| 2010/0125310 A1 | 5/2010 | Wilson et al. | |
| 2010/0125313 A1 | 5/2010 | Lee et al. | |
| 2010/0198298 A1 | 8/2010 | Glukovsky et al. | |
| 2010/0211131 A1 | 8/2010 | Williams et al. | |
| 2010/0241195 A1 | 9/2010 | Meadows et al. | |
| 2010/0244580 A1 | 9/2010 | Uchida et al. | |
| 2010/0249875 A1 | 9/2010 | Kishawi et al. | |
| 2010/0312320 A1 | 9/2010 | Faltys et al. | |
| 2010/0280568 A1 | 11/2010 | Bulkes et al. | |
| 2010/0305392 A1 | 12/2010 | Gross et al. | |
| 2010/0324630 A1 | 12/2010 | Lee et al. | |
| 2011/0034782 A1 | 2/2011 | Sugimachi et al. | |
| 2011/0046696 A1 | 2/2011 | Barolat et al. | |
| 2011/0087337 A1 | 4/2011 | Forsell | |
| 2011/0093036 A1 | 4/2011 | Mashiach | |
| 2011/0112605 A1 | 5/2011 | Fahey | |
| 2011/0137365 A1 | 6/2011 | Ben-Erza et al. | |
| 2011/0152965 A1 | 6/2011 | Mashiach | |
| 2011/0160792 A1 | 6/2011 | Fishel | |
| 2011/0160793 A1 | 6/2011 | Gindele | |
| 2011/0160798 A1 | 6/2011 | Ackermann et al. | |
| 2011/0208260 A1 | 8/2011 | Jacobson | |
| 2011/0208271 A1 | 8/2011 | Dobak | |
| 2011/0224744 A1 | 9/2011 | Moffitt et al. | |
| 2011/0224769 A1 | 9/2011 | Spenser et al. | |
| 2011/0230922 A1 | 9/2011 | Fishel | |
| 2011/0270339 A1 | 11/2011 | Murray et al. | |
| 2011/0282412 A1 | 11/2011 | Glukhovsky et al. | |
| 2011/0301662 A1 | 12/2011 | Bar-Yoseph et al. | |
| 2011/0301670 A1 | 12/2011 | Gross | |
| 2012/0004709 A1 | 1/2012 | Chen et al. | |
| 2012/0010694 A1 | 1/2012 | Lutter et al. | |
| 2012/0035679 A1 | 2/2012 | Dagan et al. | |
| 2012/0041511 A1 | 2/2012 | Lee | |
| 2012/0041514 A1 | 2/2012 | Gross et al. | |
| 2012/0065701 A1 | 3/2012 | Cauller | |
| 2012/0083857 A1 | 4/2012 | Bradley et al. | |
| 2012/0101326 A1 | 4/2012 | Simon et al. | |
| 2012/0123498 A1 | 5/2012 | Gross | |
| 2012/0130448 A1 | 5/2012 | Woods et al. | |
| 2012/0130463 A1 | 5/2012 | Ben-David et al. | |
| 2012/0158081 A1 | 6/2012 | Gross et al. | |
| 2012/0215285 A1 | 8/2012 | Tahmasian et al. | |
| 2012/0256494 A1* | 10/2012 | Kesler | H02J 50/60 307/104 |
| 2012/0296389 A1 | 11/2012 | Fang et al. | |
| 2013/0006326 A1 | 1/2013 | Ackermann et al. | |
| 2013/0066393 A1 | 3/2013 | Gross et al. | |
| 2013/0192611 A1 | 8/2013 | Taepke, II et al. | |
| 2013/0289662 A1* | 10/2013 | Olson | H02J 50/12 607/61 |
| 2013/0325084 A1 | 12/2013 | Lee | |
| 2014/0031840 A1* | 1/2014 | Mashiach | H02J 7/025 606/148 |
| 2014/0031903 A1 | 1/2014 | Mashiach | |
| 2014/0184150 A1* | 7/2014 | Walley | H02J 50/12 320/108 |
| 2014/0214134 A1 | 7/2014 | Peterson | |
| 2014/0296940 A1 | 10/2014 | Gross | |
| 2015/0004709 A1 | 1/2015 | Nazarpoor | |
| 2015/0018598 A1 | 1/2015 | Nabutovsky et al. | |
| 2015/0018728 A1 | 1/2015 | Gross et al. | |
| 2015/0039046 A1 | 2/2015 | Gross | |
| 2015/0080979 A1 | 3/2015 | Lasko et al. | |
| 2015/0100109 A1 | 4/2015 | Feldman et al. | |
| 2015/0148861 A1 | 5/2015 | Gross | |
| 2015/0148878 A1 | 5/2015 | Yoo et al. | |
| 2015/0174406 A1 | 6/2015 | Lamensdorf et al. | |
| 2015/0202449 A1 | 7/2015 | Chen | |
| 2015/0258339 A1 | 9/2015 | Burchiel et al. | |
| 2015/0270719 A1* | 9/2015 | Kurs | H02J 5/005 320/108 |
| 2015/0335882 A1 | 11/2015 | Gross et al. | |
| 2016/0206882 A1 | 7/2016 | Oron et al. | |
| 2016/0206889 A1 | 7/2016 | Plotkin et al. | |
| 2016/0206890 A1 | 7/2016 | Oron et al. | |

(56) References Cited

U.S. PATENT DOCUMENTS

| | | | |
|---|---|---|---|
| 2016/0294366 A1* | 10/2016 | Bao | G05F 3/24 |
| 2016/0361544 A1 | 12/2016 | Oron et al. | |
| 2017/0007829 A1 | 1/2017 | Gross | |
| 2017/0128724 A1 | 5/2017 | Oron et al. | |
| 2017/0136232 A1 | 5/2017 | Oron et al. | |
| 2017/0224996 A1 | 8/2017 | Oron et al. | |
| 2017/0232255 A1 | 8/2017 | Kent et al. | |
| 2017/0296426 A1 | 10/2017 | Oron et al. | |
| 2018/0353764 A1 | 12/2018 | Oron et al. | |
| 2020/0046974 A1 | 2/2020 | Ostroff et al. | |

FOREIGN PATENT DOCUMENTS

| | | |
|---|---|---|
| EP | 1533000 | 5/2005 |
| EP | 1703638 | 11/2012 |
| WO | 1998/010832 | 3/1998 |
| WO | 1999/026530 | 6/1999 |
| WO | 01/10432 | 2/2001 |
| WO | 2001/010375 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 | 7/2013 |
| WO | 2013/111137 | 8/2013 |
| WO | 2013/156038 | 10/2013 |
| WO | 2013/164829 | 11/2013 |
| WO | 2014/081978 | 5/2014 |
| WO | 2014/087337 | 6/2014 |
| WO | 2014/167568 | 10/2014 |
| WO | 2015/004673 | 1/2015 |
| WO | 2016/028608 | 2/2016 |
| WO | 2016/157183 | 10/2016 |
| WO | 2016/172109 | 10/2016 |

OTHER PUBLICATIONS

An Office Action dated Jun. 17, 2021, which issued during the prosecution of U.S. Appl. No. 16/363,256.
An Office Action dated Dec. 5, 2018, which issued during the prosecution of U.S. Appl. No. 15/581,390.
An Office Action dated Jun. 26, 2019, which issued during the prosecution of U.S. Appl. No. 15/395,257.
An Office Action dated Feb. 7, 2019, which issued during the prosecution of U.S. Appl. No. 15/706,956.
Alo, Kenneth M., et al. "Lumbar and sacral nerve root stimulation (NRS) in the treatment of chronic pain: a novel anatomic approach and neuro stimulation technique." Neuromudulation: Technology at the Neural Interface 2.1 (1999): 23-31.
Gofeld, Michael, and John G. Hanlon. "Ultrasound-Guided Placement of a Paddle Lead Onto Peripheral Nerves: Surgical Anatomy and Methodology." Neuromodulation: Technology at the Neural Interface 17.1 (2014): 48-53.
Stuart, R. Morgan, and Christopher J. Winfree. "Neurostimulation techniques for painful peripheral nerve disorders." Neurosurgery Clinics of North America 20.1 (2009): 111-120.
An Office Action dated Dec. 21, 2020, which issued during the prosecution of U.S. Appl. No. 16/363,256.
An Office Action dated Dec. 2, 2020, which issued during the prosecution of U.S. Appl. No. 16/166,383.
C. de Balthasar, G. Cosendai, M. Hansen, D. Canfield, L. Chu, R. Davis, and J. Schulman, "Attachment of leads to RF-BION® microstimulators." Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).
Chris Seper, "Neuros Medical Launches to Develop New Device to Block Amputee, Chronic Pain", Mar. 17, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.

(56) References Cited

OTHER PUBLICATIONS

An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/050069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).

M. Devor, "Pain Networks", Handbook of Brand Theory and Neural Networks, ED M.A. Arbib MIT Press pp. 696-701, 1998.
Epilepsy center. http://www.bcm.tmc.edu/neural/struct/epilep/epilpsy_vagus.html.
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 lssue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
U.S. Appl. No. 61/591,024, filed Jan. 26, 2012.
Mortimer et al., Peripheral Nerve and Muscle Stimulation, Neuroprosthetics Theory and Practice, Chapter 4.2, 2004, p. 632-638.
An Office Action dated May 19, 2017, which issued during the prosecution of U.S. Appl. No. 14/935,941.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
A Notice of Allowance dated Jun. 9, 2014, which issued during the prosecution of U.S. Appl. No. 12/796,102.
Notice of Allowance dated Sep. 1, 2017, which issued during the prosecution of U.S. Appl. No. 14/649,873.
Brindley (1983) A technique for anodally blocking large nerve fibers.
An Office Action dated Sep. 22, 2016, which issued during the prosecution of U.S. Appl. No. 14/374,375.
DJOGlobal.com—Interferential Current Therapy (IFC).
A Notice of Allowance dated Apr. 25, 2014, which issued during the prosecution of U.S. Appl. No. 13/528,433.
U.S. Appl. No. 61/662,073, filed Jun. 20, 2012.
An Office Action dated Sep. 26, 2013, which issued during the prosecution of U.S. Appl. No. 13/528,433.
U.S. Appl. No. 60/985,353, filed Nov. 5, 2007.
Notice of Allowance dated Jun. 1, 2017, which issued during the prosecution of U.S. Appl. No. 14/601,626.
electrotherapy.org—Interferential Therapy.
Notice of Allowance dated May 17, 2017, which issued during the prosecution of U.S. Appl. No. 14/601,626.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Notice of Allowance dated Nov. 4, 2016, which issued during the prosecution of U.S. Appl. No. 14/601,568.

(56) References Cited

OTHER PUBLICATIONS

Sinan Filiz, Luke Xie, Lee E. Weiss, O.B. Ozdoganlar, Micromilling of microbarbs for medical implants, International Journal of Machine Tools and Manufacture, vol. 48, Issues 3-4, Mar. 2008, pp. 459-472.
UCLA Team Reports Initial Success with Trigeminal Nerve Stimulation epilepsy. https://web.archive.org/web/20121020145122/https://www.epilepsy.com/epilepsy/newsletter/apr09_STIM.
Kucklick, Theodore R., ed. *The medical device R&D handbook*. Chapter 3—Intro to needles and cannulae. CRC Press, 2012.
Szmurlo, R., Starzynski, J., Wincenciak, S. and Rysz, A. (2009) 'Numerical model of vagus nerve electrical stimulation', *COMPEL—The international journal for computation and mathematics in electrical and electronic engineering*, 28(1), pp. 211-220.
An Office Action dated Apr. 5, 2017, which issued during the prosecution of U.S. Appl. No. 14/374,375.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
Reggiani et al. "Biophysical effects of high frequency electrical field on muscle fibers in culture." (2009) pp. 49-56.
https://www.uroplasty.com/files/pdf/20158.pdf Brochure (Downloaded Oct. 16, 2014).
An Office Action dated Aug. 8, 2016, which issued during the prosecution of U.S. Appl. No. 14/735,741.
An International Search Report and a Written Opinion both dated Jul. 11, 2013, which issued during the prosecution of Applicant's PCT/IL2013/050069.
An International Search Report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
An Office Action dated Dec. 12, 2016, which issued during the prosecution of U.S. Appl. No. 14/939,418.
Ex Parte Quayle Action dated Sep. 14, 2016, which issued during the prosecution of U.S. Appl. No. 14/601,568.
An Office Action dated May 13, 2016, which issued during the prosecution of U.S. Appl. No. 14/601,568.
An Office Action dated Aug. 11, 2016, which issued during the prosecution of U.S. Appl. No. 14/601,626.
CBS news article entitled, "Migraine 'smart' patch tested to help ease pain" by Steven Reinberg.
Zhang, D., Zhang, Z., Zi, Z., Zhang, Y., Zeng, W. and Chu, P.K., 2008. Fabrication of graded TiN coatings on nitinol occluders and effects on in vivo nickel release. Bio-medical materials and engineering, 18(6), pp. 387-393—an abstract.
Cardiovascular Stents as Antennas for Implantable Wireless Applications, by Ebrish, BMEN 5151, Apr. 29, 2010.
An Office Action dated Nov. 21, 2016, which issued during the prosecution of U.S. Appl. No. 14/601,626.
Spinal Cord Stimulation advanced level (Mayfield clinic)—dated Feb. 2010.
European Search Report dated Feb. 3, 2017, which issued during the prosecution of Applicant's European App No. 16196878.9.
Amendment in Response to Official Action dated Jan. 24, 2019 from the United States Patent and Trademark Office in U.S. Appl. No. 15/621,433.
An Office Action dated Dec. 6, 2017, which issued during the prosecution of U.S. Appl. No. 14/601,604.
An Office Action dated Dec. 26, 2017, which issued during the prosecution of U.S. Appl. No. 14/935,941.
An Office Action dated Jan. 8, 2018, which issued during the prosecution of U.S. Appl. No. 14/935,941.
An Office Action dated Mar. 5, 2018, which issued during the prosecution of U.S. Appl. No. 15/360,501.
An Office Action dated Nov. 30, 2017, which issued during the prosecution of U.S. Appl. No. 15/726,971.
Abkenari, Lara Dabiri, et al. "Clinical experience with a novel subcutaneous implantable defibrillator system in a single center." *Clinical Research in Cardiology* 100.9 (2011): 737-744.
St. Jude Medical, Inc. fact sheet entitled, "Peripheral Nerve Stimulation for Intractable Chronic Migraine".
Automatic Impedance Matching for 13.56 MHz NFC Antennas In Proceedings of the 6th Symposium on Communication Systems, Networks and Digital Signal Processing (2008) by Michael Roland, Harald Witschnig, Christian Saminger.
Takahata, K.; DeHennis, A.; Wise, K.D.; Gianchandani, Y.B., "Stentenna: a micromachined antenna stent for wireless monitoring of implantable microsensors," in *Engineering in Medicine and Biology Society, 2003. Proceedings of the 25th Annual International Conference of the IEEE*, vol. 4, No., pp. 3360-3363 vol. 4, 17-21.
Itchkawitz—OC TechInnovation Blog—Electrodes for implantable defibrillator. Printout from http://octechinnovation.com/tag/cameron-health (Downloaded Mar. 2012).
Kaszala, K. and Ellenbogen, K.A., 2010. Device sensing sensors and algorithms for pacemakers and implantable cardioverter defibrillators. Circulation, 122(13), pp. 1328-1340.
An Office Action dated Apr. 22, 2019, which issued during the prosecution of U.S. Appl. No. 15/638,924.
An Office Action dated Oct. 11, 2018, which issued during the prosecution of U.S. Appl. No. 15/638,924.
Notice of Allowance dated Jan. 17, 2020, which issued during the prosecution of U.S. Appl. No. 15/638,924.
An Interview Summary dated Mar. 5, 2019, which issued during the prosecution of U.S. Appl. No. 15/638,924.
An Advisory Action and an Interview Summary dated Sep. 16, 2019, which issued during the prosecution of U.S. Appl. No. 15/638,924.
An Office Action dated Jan. 24, 2019, which issued during the prosecution of U.S. Appl. No. 15/621,433.
An Office Action dated Jul. 9, 2019, which issued during the prosecution of U.S. Appl. No. 15/621,433.
An Office Action dated Oct. 30, 2018, which issued during the prosecution of U.S. Appl. No. 15/621,433.

* cited by examiner

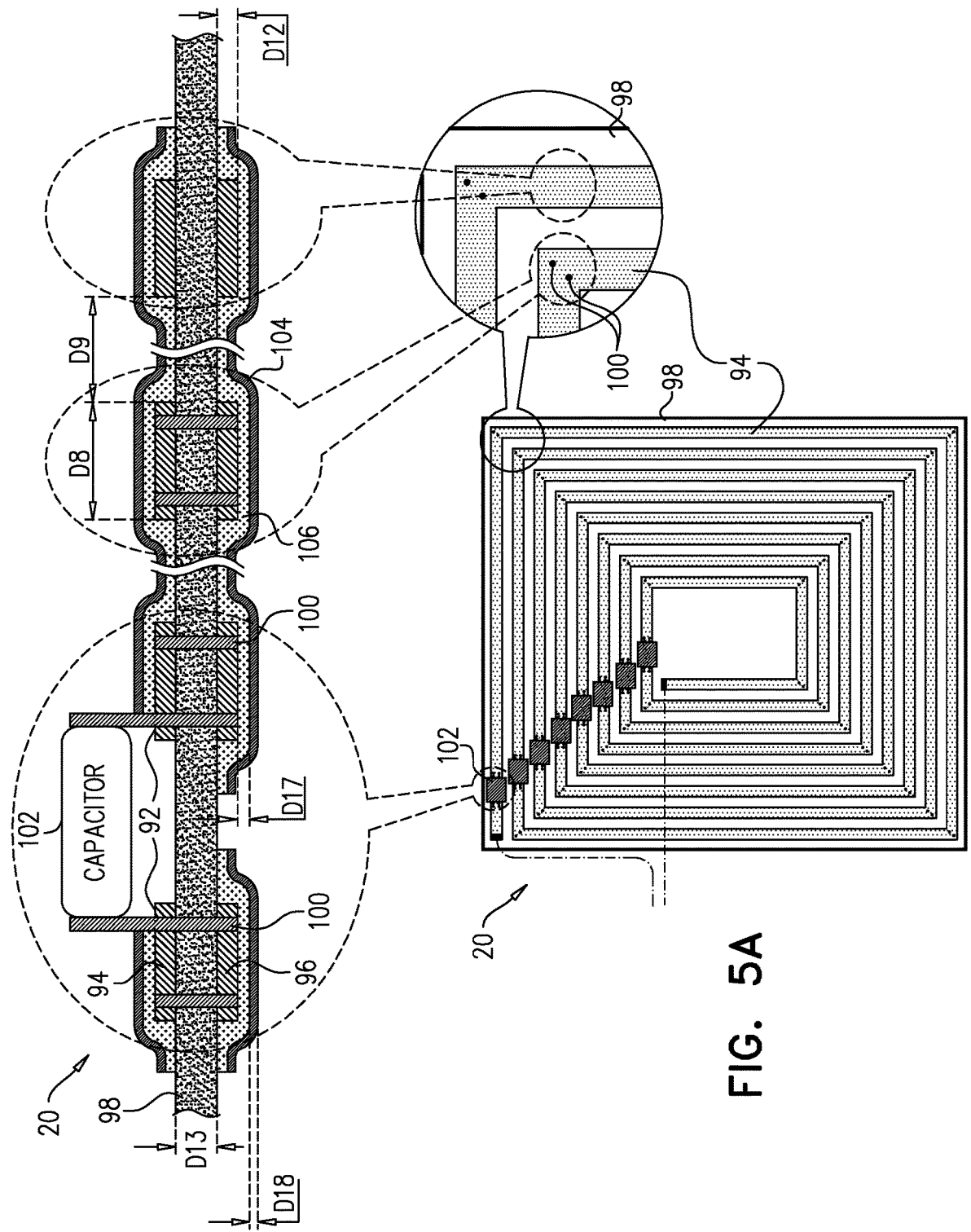

ANTENNA CONFIGURATION

CROSS-REFERENCE TO RELATED APPLICATIONS

The present application is a Continuation of U.S. Ser. No. 16/737,253 to Oron et al., entitled "Antenna configuration," which published as U.S. 2020/0,139,136, and which is a Divisional of U.S. Ser. No. 15/621,433 to Oron et al. (abandoned), filed Jun. 13, 2017, entitled, "Antenna configuration."

FIELD OF THE INVENTION

Applications of the present invention relate to transmitting power to an implanted medical device.

BACKGROUND

Electrical power can be transferred to a percutaneous medical implant by magnetic induction. A current flowing through a coil produces a magnetic field, which, in turn, will induce a current in a second coil, provided the second coil is in close enough proximity to the magnetic field and oriented such that the magnetic field is substantially parallel to the central longitudinal axis of the second coil. A coil inside a medical implant can therefore act as a receiving coil, while a coil outside a patient's body can act as a transmitting coil. A current can be driven through the transmitting coil in order to induce an induced current in the receiving coil, thereby powering the medical implant.

A CBS News article entitled "Migraine 'smart' patch tested to help ease pain," by Steven Reinberg, describes a study performed at Rambam Medical Center in Haifa, Israel, under Dr. David Yarnitzky, chair of neurology at the Rambam Medical Center. The study tested an arm patch to be worn on the upper arm with "[r]ubber electrodes and a chip in the patch [to] produce electric impulses that block pain signals from reaching the brain," in order to treat migraine pain.

A St. Jude Medical, Inc. fact sheet entitled "Peripheral nerve stimulation for intractable chronic migraine," describes peripheral nerve stimulation as a treatment for chronic migraines. The fact sheet states that "Peripheral nerve stimulation (PNS) is a therapy that uses mild electrical pulses to stimulate the nerves of the peripheral nervous system. The peripheral nerves make up a network of nerves outside of the central nervous system. For example, the ulnar nerve in the arms and the sciatic nerve in the legs are part of the peripheral nervous system. The St. Jude Medical systems currently approved for PNS in select markets look and operate much like a cardiac pacemaker. However, instead of sending pulses to the heart, the pulses are carried to the occipital nerves, located in the back of the head . . . . Researchers believe that by delivering electrical pulses to these specific peripheral nerve fibers, PNS may influence the way the nerves communicate with the brain and provide an alternative to long-term drug therapy for the relief of chronic migraine."

SUMMARY OF THE INVENTION

A method is described for transmitting power to a medical implant that includes a receiving coil. For some applications, a transmitting coil, disposed in a transmitting coil housing, is placed against skin of a subject such that a central longitudinal axis of the transmitting coil is substantially perpendicular to the skin. For some applications, the medical implant is implanted between an ankle and a knee of a leg of a subject, typically closer to the ankle than the knee. To increase efficiency of the power transfer while accommodating for limited space near the ankle, the transmitting coil is oriented with respect to the skin such that it is not centered over the receiving coil, but rather only a portion of the transmitting coil is disposed directly over the receiving coil. This orientation of the transmitting coil with respect to the receiving coil allows for powering the medical implant using only one transmitting coil. To transmit power to the medical implant, control circuitry is activated to drive a current through the transmitting coil that induces an induced current in the receiving coil.

Typically, the transmitting coil housing and the transmitting coil are flexible in order to comfortably conform to the shape of a limb of the subject. In the absence of any forces applied to the transmitting coil, the transmitting coil has a nominal resonance frequency. In order to accommodate for possible fluctuations in the resonance frequency of the transmitting coil due to the flexing, a sensor may be coupled to the control circuitry and configured to determine an extent of divergence of (a) the resonance frequency of the transmitting coil when the transmitting coil is flexed from (b) the nominal resonance frequency of the transmitting coil, occurring in the absence of any forces applied to the transmitting coil. The control circuitry is further configured to output a signal that controls one or more electrical components that are (a) coupled to the control circuitry and (b) configured to tune the resonance frequency of the transmitting coil in order to compensate for the fluctuations.

There is therefore provided, in accordance with some applications of the present invention, a method for transmitting power to a medical implant that includes a receiving coil that is oriented such that a longitudinal axis of the receiving coil is substantially parallel to skin of a subject, the method including:

providing a transmitting coil disposed in a housing;
placing the housing against the skin such that:
(a) a central longitudinal axis of the transmitting coil is substantially perpendicular to the skin,
(b) a portion of the transmitting coil is disposed over the receiving coil,
(c) a first distance, from the central longitudinal axis of the transmitting coil to a longitudinal center of the receiving coil, is greater than a second distance, from the central longitudinal axis of the transmitting coil to an inner edge of the portion of the transmitting coil, and
(d) the first distance is less than a third distance, from the central longitudinal axis of the transmitting coil to an outer edge of the portion of the transmitting coil; and
activating control circuitry to power the medical implant by driving a current through the transmitting coil that induces an induced current in the receiving coil.

For some applications, placing includes identifying the subject as suffering from migraines or cluster headaches, and in response to the identifying, placing the housing on a leg of a subject such that:

(a) the transmitting coil is disposed between a knee and an angle of the leg, and
(b) the transmitting coil transmits power to a medical implant configured to stimulate a tibial nerve in the leg of the subject.

For some applications, placing includes placing the housing on a leg of the subject such that:

(a) the transmitting coil is disposed between a knee and an ankle of the leg, and (b) (i) a portion of the transmitting coil that is disposed over the receiving coil is closer to the ankle than (ii) a portion of the transmitting coil that is disposed at 180 degrees from the portion of the transmitting coil that is disposed over the receiving coil, is to the ankle.

For some applications, placing includes placing the housing such that the first distance is 15-45 mm.

For some applications, placing includes placing the housing such that the second distance is less than 30 mm.

For some applications, placing includes placing the housing such that the third distance is 40-60 mm.

For some applications, placing includes placing the housing such that a difference between the third distance and the second distance is 30-40 mm.

For some applications, providing the transmitting coil includes providing a transmitting coil wherein a ratio of (a) a difference between the third distance and the second distance, to (b) a longitudinal length of the receiving coil is greater than 0.5.

For some applications, providing the transmitting coil includes providing a transmitting coil wherein a ratio of (a) a difference between the third distance and the second distance, to (b) a longitudinal length of the receiving coil is less than 1.5.

For some applications, providing the transmitting coil includes providing a transmitting coil wherein a ratio of (a) a difference between the third distance and the second distance, to (b) a longitudinal length of the receiving coil is between 0.5 and 1.5.

For some applications, providing the transmitting coil includes providing a transmitting coil wherein:

(a) a height of the transmitting coil measured along a longitudinal axis of the transmitting coil is 300-600 microns, (b) an outer diameter of the transmitting coil is 100-140 mm, and (c) a ratio of the outer diameter of the transmitting coil to the height of the transmitting coil is at least 150.

For some applications, placing includes placing the housing such that the transmitting coil is over a receiving coil, wherein:

(a) a longitudinal length of the receiving coil is 3-15 mm, (b) an outer diameter of the receiving coil is 0.6-1.5 mm, and (c) a ratio of the outer diameter of the receiving coil to the longitudinal length of the receiving coil is less than 0.5.

For some applications, activating the control circuitry includes activating the control circuitry to drive the current through the transmitting coil at a frequency of 1-20 MHz.

For some applications, placing includes placing the housing against the skin and subsequently sliding it along the skin until an indicator, coupled to the housing, indicates that the transmitting coil is in an acceptable position with respect to the receiving coil.

For some applications, providing the transmitting coil includes providing a transmitting coil wherein a cross-sectional area of a wire of the transmitting coil is rectangular, wherein the cross-section is taken perpendicular to a direction of current flow within the wire.

For some applications, providing the transmitting coil includes providing a transmitting coil that is elongated in a direction perpendicular to the central longitudinal axis of the receiving coil.

For some applications, providing the transmitting coil includes providing a planar coil disposed in a housing.

For some applications, providing the planar coil includes providing a planar coil including a plurality of layers.

For some applications, providing the planar coil includes providing a planar coil with a line spacing, of adjacent coplanar wires, of 0.25-3 mm.

For some applications, providing the planar coil includes providing a planar coil with a line width of 1-4 mm.

For some applications, providing the transmitting coil includes providing a transmitting coil wherein an average distance from a wire of the transmitting coil to the central longitudinal axis of the transmitting coil is less than two times a square root of a cross-sectional area of a central non-coiled region of the transmitting coil.

For some applications, providing includes providing a transmitting coil wherein an average distance from the wire of the transmitting coil to the central longitudinal axis of the transmitting coil is 0.6-1.5 times the square root of the cross-sectional area of the central non-coiled region of the transmitting coil.

There is further provided, in accordance with some applications of the present invention, apparatus including:

a medical implant, the medical implant including:

a receiving coil; and a plurality of electrodes;

a transmitting coil, having wire disposed at all rotational locations about a central longitudinal axis of the transmitting coil, oriented such that:

(a) the central longitudinal axis of the transmitting coil is substantially perpendicular to a central longitudinal axis of the receiving coil, (b) at one of the rotational locations, a line from the wire and substantially parallel to the central longitudinal axis of the transmitting coil intersects the receiving coil, and at 180 degrees from the rotational location a line from the wire and substantially parallel to the central longitudinal axis of the transmitting coil does not intersect the receiving coil, (c) a first distance from the central longitudinal axis of the transmitting coil to a longitudinal center of the receiving coil, is greater than a second distance from the central longitudinal axis of the transmitting coil to an inner edge of the transmitting coil at the one of the rotational locations, and (d) the first distance is less than a third distance from the central longitudinal axis of the transmitting coil to an outer edge of the transmitting coil at the one of the rotational locations; and control circuitry configured to transmit power to the medical implant by driving a current through the transmitting coil that induces an induced current in the receiving coil.

For some applications, the control circuitry is configured to drive the current through the transmitting coil at a frequency of 1-20 MHz.

For some applications, the medical implant is configured to be implanted 1-5 cm below skin of a subject, and the control circuitry is configured to transmit the power, by driving the current through the transmitting coil that induces the induced current in the receiving coil, when the medical implant is implanted 1-5 cm below the skin.

For some applications, the receiving coil is a cylindrical coil including a ferrite core.

For some applications, the first distance is 15-45 mm.

For some applications, the second distance is less than 30 mm.

For some applications, the third distance is 40-60 mm.

For some applications, a difference between the third distance and the second distance is 30-40 mm.

For some applications, a ratio of (a) a difference between the third distance and the second distance, to (b) a longitudinal length of the receiving coil is greater than 0.5.

For some applications, a ratio of (a) a difference between the third distance and the second distance, to (b) a longitudinal length of the receiving coil is less than 1.5.

For some applications, a ratio of (a) a difference between the third distance and the second distance, to (b) a longitudinal length of the receiving coil is between 0.5 and 1.5.

For some applications:
(a) a height of the transmitting coil measured along a longitudinal axis of the transmitting coil is 300-600 microns,
(b) an outer diameter of the transmitting coil is 100-140 mm, and
(c) a ratio of the outer diameter of the transmitting coil to the height of the transmitting coil is at least 150.

For some applications:
(a) a longitudinal length of the receiving coil is 3-15 mm,
(b) an outer diameter of the receiving coil is 0.6-1.5 mm, and
(c) a ratio of the outer diameter of the receiving coil to the longitudinal length of the receiving coil is less than 0.5.

For some applications:
(a) a first ratio, of the outer diameter of the transmitting coil to a height of the transmitting coil measured along a longitudinal axis of the transmitting coil, is at least 150,
(b) a second ratio, of the outer diameter of the receiving coil to the longitudinal length of the receiving coil, is less than 0.5, and
(c) a ratio of the first ratio to the second ratio is at least 300.

For some applications, the transmitting coil has between 4 and 10 turns.

For some applications, the receiving coil has between 10 and 40 turns.

For some applications, the medical implant is configured to send a signal to the control circuitry upon receiving the transmitted power.

For some applications, a cross-sectional area of a wire of the transmitting coil is rectangular, the cross-section being taken perpendicular to a direction of current flow within the wire.

For some applications, the transmitting coil is elongated in a direction perpendicular to the central longitudinal axis of the receiving coil.

For some applications, a length of the receiving coil is 3-15 mm.

For some applications, the medical implant includes a housing having a length of 30-45 mm and the receiving coil is disposed in within the housing.

For some applications, the apparatus further includes an indicator, and the control circuitry is configured to activate the indicator upon the transmitting coil being in an acceptable position with respect to the receiving coil.

For some applications, the control circuitry is configured to detect interference with its output signal and to activate the indicator upon the detection of the interference.

For some applications, the control circuitry is configured to activate the indicator again, upon the transmitting coil no longer being in correct position with respect to the receiving coil.

For some applications, the control circuitry is configured to ascertain an indication of an efficiency of the power transfer between the transmitting coil and the receiving coil, and to activate the indicator according to the ascertaining.

For some applications, the control circuitry is configured to measure a loss of power in the transmitting coil, the loss of power being indicative of the efficiency of the power transfer.

For some applications, the transmitting coil is a planar coil.

For some applications, a line width of the transmitting coil is 1-4 mm.

For some applications, the planar coil includes a plurality of layers.

For some applications, a line spacing of adjacent coplanar wires in the transmitting coil is 0.25-3 mm.

For some applications, the apparatus further includes a flexible printed circuit board (PCB), and the transmitting coil includes two planar layers disposed on either side of the flexible PCB.

For some applications, a height of each layer measured along a longitudinal axis of the transmitting coil is 15-100 microns.

For some applications, a height of the flexible PCB measured along a longitudinal axis of the transmitting coil is 100-200 microns.

For some applications, respective wires of the two layers are conductively connected to each other at at least one location along each turn of the transmitting coil.

For some applications, the apparatus further includes at least one capacitor, coupled to the transmitting coil at at least one location along at least one turn of the transmitting coil.

For some applications, the capacitor is electrically coupled to both of the two layers.

For some applications, the apparatus further includes a plurality of capacitors coupled to the transmitting coil such that at least one capacitor is coupled to the transmitting coil at at least one location along each turn of the transmitting coil.

For some applications, each of the capacitors is electrically coupled to both of the two layers.

For some applications, an insulating cover is coupled to both layers of the transmitting coil disposed on the flexible PCB.

For some applications, an average distance from a wire of the transmitting coil to the central longitudinal axis of the transmitting coil is less than two times a square root of a cross-sectional area of a central non-coiled region of the transmitting coil.

For some applications, the average distance from the wire of the transmitting coil to the central longitudinal axis of the transmitting coil is 0.6-1.5 times the square root of the cross-sectional area of the central non-coiled region of the transmitting coil.

There is further provided, in accordance with some applications of the present invention, apparatus for use with a medical implant that includes a receiving coil, the apparatus including:
a flexible housing configured to be placed against skin of a subject;
a flexible transmitting coil disposed in the housing;
control circuitry configured to transmit power to the medical implant by driving a current through the transmitting coil that induces an induced current in the receiving coil;
a sensor coupled to the control circuitry, the sensor configured to determine an extent of divergence of (a) a resonance frequency of the transmitting coil when the transmitting coil is flexed from (b) a nominal resonance frequency of the transmitting coil, occurring in the absence of any forces applied to the transmitting coil, and configured to output a signal according to the determination; and one or more electrical components, coupled to the control circuitry and configured to tune the resonance frequency of the transmitting coil in response to the determination of the sensor.

For some applications, the control circuitry is configured to set the frequency of the current output by the control circuitry to be between 1 and 20 MHz.

For some applications, the flexible transmitting coil is configured to flex such that it can substantially conform to a lateral wall of a cylinder having a diameter between 8 and 50 cm.

For some applications, the sensor includes a phase detector, configured to (a) determine a phase difference between the phase of the current output by the control circuitry, and the phase of either a current or a voltage on at least one component of the transmitting coil, the phase difference being due to flexing of the transmitting coil, and (b) output a signal according to the determination.

For some applications, the control circuitry includes a feedback calculator configured to:

(a) receive the signal output by the phase detector, (b) determine, according to the signal output by the phase detector, a necessary change in the resonance frequency of the transmitting coil, in order to reduce the extent of divergence of (a) the resonance frequency of the transmitting coil when the transmitting coil is flexed from (b) the nominal resonance frequency of the transmitting coil, and (c) output a signal to the one or more electrical components, according to the determination.

For some applications, the sensor is configured to:

(a) measure a parameter that is indicative of the frequency of the current output by the control circuitry and the resonance frequency of the transmitting coil, (b) look up at least one value in a look-up table with respect to the measured parameter, and (c) output a signal to the one or more electrical components based on the looked-up value.

For some applications, the control circuitry is configured such that the measured parameter is a level of power output by the transmitting coil.

For some applications, at least one of the one or more electrical components is a variable inductor, the control circuitry is configured to vary an inductance of the variable inductor according to the signal output by the sensor, and the resonance frequency of the transmitting coil varies according to the variation of the inductance of the variable inductor.

For some applications, at least one of the one or more electrical components is a variable capacitor, the control circuitry is configured to vary a capacitance of the variable capacitor according to the signal output by the sensor, and the resonance frequency of the transmitting coil varies according to the variation of the capacitance of the variable capacitor.

For some applications, the apparatus further includes a plurality of switches, each switch coupled to a respective one of the electrical components.

For some applications, the control circuitry is configured to tune the resonance frequency of the transmitting coil, according to the signal output by the sensor, by activating at least one of the plurality of switches to facilitate or inhibit current flow through the respective electrical component.

For some applications, the control circuitry is configured to dither the resonance frequency of the transmitting coil by repeatedly activating and deactivating the at least one of the plurality of switches to facilitate or inhibit current flow through the respective electrical component.

For some applications, at least one of the plurality of switches is configured to be manually operated and the remaining switches are configured to be operated by the control circuitry, wherein (a) the electrical component coupled to the manually-operated switch is configured to vary the resonance frequency of the transmitting coil by more than (b) the electrical components coupled to the switches operated by the control circuitry are configured to vary the resonance frequency of the transmitting coil.

For some applications, the one or more electrical components is a plurality of inductors, coupled in series.

For some applications, the plurality of inductors includes 3-9 inductors.

For some applications, a first one of the inductors has an inductance of 1.5-2.5 times an inductance of another one of the inductors.

For some applications, the inductance of the first one of the inductors is twice the inductance of the other one of the inductors.

For some applications, each one of at least half of the inductors has an inductance which is twice an inductance of another one of the inductors.

For some applications, the control circuitry is configured such that when the extent of divergence of (a) the resonance frequency of the transmitting coil when the transmitting coil is flexed from (b) the nominal resonance frequency of the transmitting coil is reduced, current is allowed to pass through at least one of the inductors and current is inhibited from passing through at least another one of the inductors.

For some applications, the one or more electrical components is a plurality of capacitors coupled in parallel.

For some applications, the plurality of capacitors includes 4 to 10 capacitors.

For some applications, a first one of the capacitors has a capacitance of 1.5-2.5 times a capacitance of another one of the capacitors.

For some applications, the capacitance of the first one of the capacitors is twice the capacitance of the other one of the capacitors.

For some applications, each one of at least half of the capacitors has a capacitance that is twice a capacitance of another one of the capacitors.

For some applications, the control circuitry is configured such that when the extent of divergence of (a) the resonance frequency of the transmitting coil when the transmitting coil is flexed from (b) the nominal resonance frequency of the transmitting coil is reduced, current is allowed to pass through at least one of the capacitors and current is inhibited from passing through at least another one of the capacitors.

For some applications, the one or more electrical components is a plurality of electrical components including inductors, coupled in series, and capacitors, coupled in parallel.

For some applications, a first one of the inductors has an inductance of 1.5-2.5 times an inductance of another one of the inductors.

For some applications, the inductance of the first one of the inductors is twice the inductance of the other one of the inductors.

For some applications, each one of at least half of the inductors has an inductance that is twice an inductance of another one of the inductors.

For some applications, a first one of the capacitors has a capacitance of 1.5-2.5 times a capacitance of another one of the capacitors.

For some applications, the capacitance of the first one of the capacitors is twice the capacitance of the other one of the capacitors.

For some applications, each one of at least half of the capacitors has a capacitance that is twice a capacitance of another one of the capacitors.

For some applications, the control circuitry is configured such that when the extent of divergence of (a) the resonance frequency of the transmitting coil when the transmitting coil is flexed from (b) the nominal resonance frequency of the transmitting coil is reduced, current is allowed to pass through at least one of the electrical components and current is inhibited from passing through at least another one of the electrical components.

For some applications:

the control circuitry is configured to activate the switches by applying a respective voltage of 30-300 volts to each switch, the switches include transistors, acting as diodes, having respective capacitances that are dependent on the respective voltage applied to each switch.

For some applications, the control circuitry is configured to apply the respective voltages to the respective switches at a voltage of 50-200 volts.

For some applications:

the control circuitry is configured to activate the switches by applying a respective voltage of 30-300 volts to each switch, and the switches include transistors, which behave in their off states as variable capacitors, having respective capacitances that are dependent on the respective voltage applied to each switch.

For some applications, the control circuitry is configured to apply the respective voltages to the respective switches at a voltage of 50-200 volts.

For some applications, the apparatus further includes the medical implant.

There is further provided, in accordance with some applications of the present invention, a method for treating a subject suffering from migraines or cluster headaches, the method including:

identifying the subject as suffering from migraines or cluster headaches; and in response to the identifying, powering a medical implant to stimulate a tibial nerve in a leg of the subject.

The present invention will be more fully understood from the following detailed description of applications thereof, taken together with the drawings, in which:

BRIEF DESCRIPTION OF THE DRAWINGS

FIGS. 5A-B are schematic illustrations of a cross-sectional view of the transmitting coil and a top view of the transmitting coil, in accordance with some applications of the present invention;

DETAILED DESCRIPTION

Figure 1A:
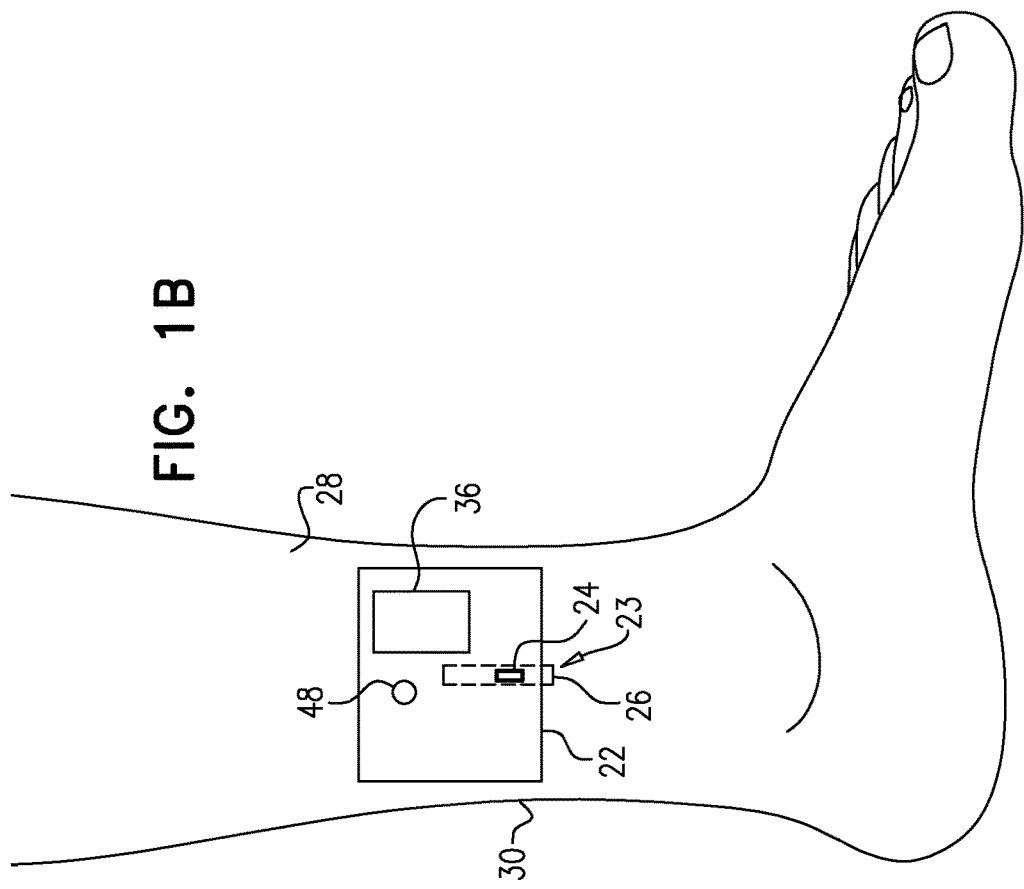
FIGS. 1A-B are schematic illustrations of a medical implant comprising a receiving coil under skin of a subject and a transmitting coil disposed in a housing that is placed against the skin, in accordance with some applications of the present invention.
Figure 1B:
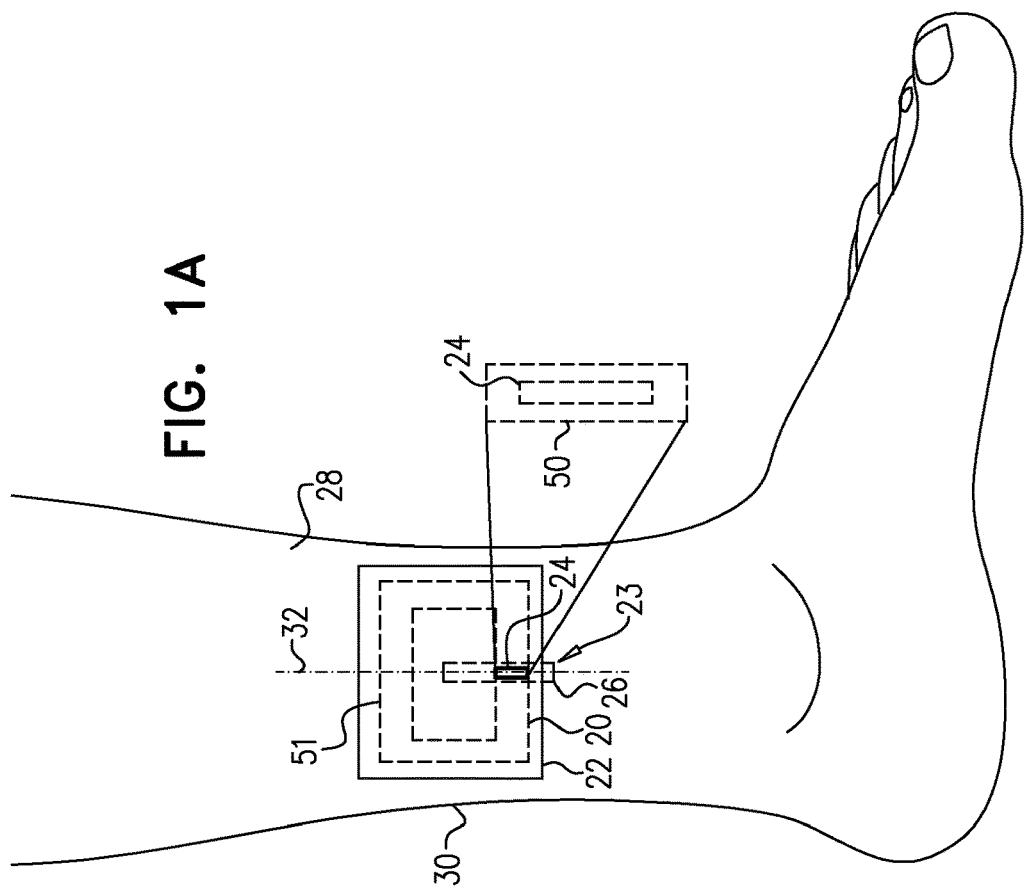

Reference is made to FIGS. 1A-B, which are schematic illustrations of a transmitting coil 20, disposed in a transmitting coil housing 22 that is placed against skin 28 of a subject, and a medical implant 23, under skin 28 of a limb 30 of a subject, comprising a receiving coil 24 that is disposed in a receiving coil housing 26, in accordance with some applications of the present invention. Typically, receiving coil housing 26 is oriented such that a central longitudinal axis 32 of receiving coil 24 is substantially parallel to skin 28. Transmitting coil housing 22 of transmitting coil 20 is typically placed against skin 28 and oriented such that a central longitudinal axis 34 (FIG. 2) of transmitting coil 20 is substantially perpendicular to skin 28. Power is transmitted to medical implant 23 by activating control circuitry 36 (FIG. 1B), coupled to transmitting coil housing 22, to drive a current through transmitting coil 20, for example at a frequency of 1-20 MHz, e.g., a fixed frequency of 6.78 or 13.56 MHz. For some applications, lower frequencies such as 0.1-0.5 MHz may also be used. A magnetic field, for example magnetic field 52 (FIG. 2A), generated by the current in transmitting coil 20, induces an induced current in receiving coil 24.

As used in the present application, including in the claims, a "central longitudinal axis" of an elongate structure is the set of all centroids of transverse cross-sectional sections of the structure along the structure. Thus, the cross-sectional sections are locally perpendicular to the central longitudinal axis, which runs along the structure. (If the structure is circular in cross-section, the centroids correspond with the centers of the circular cross-sectional sections.)

As used in the present application, including in the claims, substantially parallel elements are to be understood as having an angle between them that is less than 10 degrees. For some applications, substantially parallel elements have an angle between them that is less than 5 degrees.

As used in the present application, including in the claims, substantially perpendicular elements are to be understood as having an angle between them that is at least 85 degrees and/or less than 95 degrees.

Figure 2A:
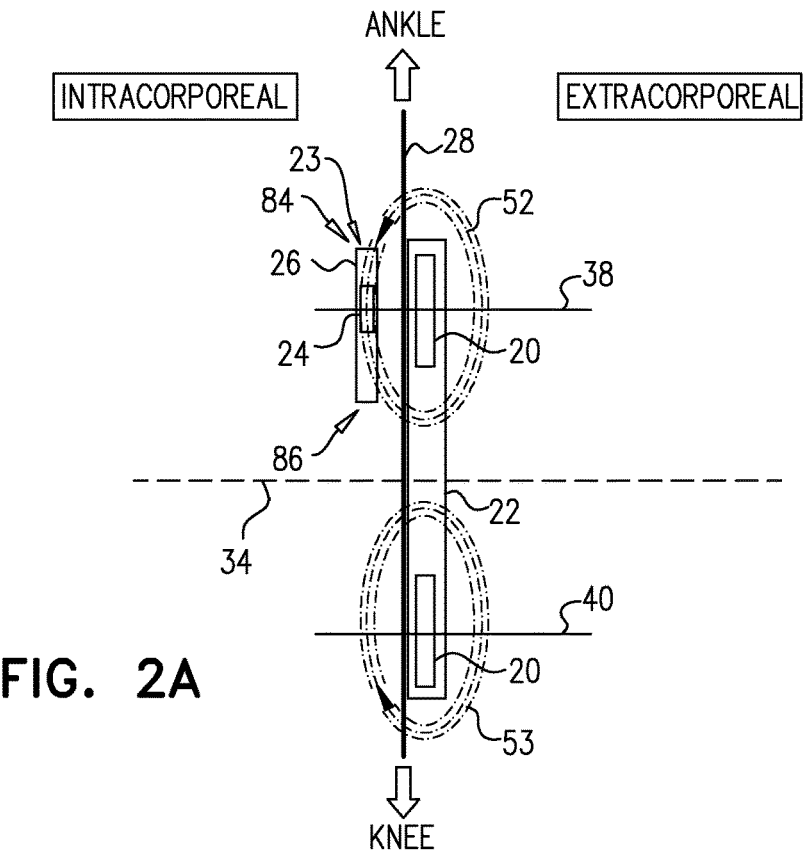
FIGS. 2A-B are schematic illustrations of a cross-sectional view of the receiving coil disposed in the medical implant and the transmitting coil disposed in the housing against the skin, in accordance with some applications of the present invention.
Figure 2B:
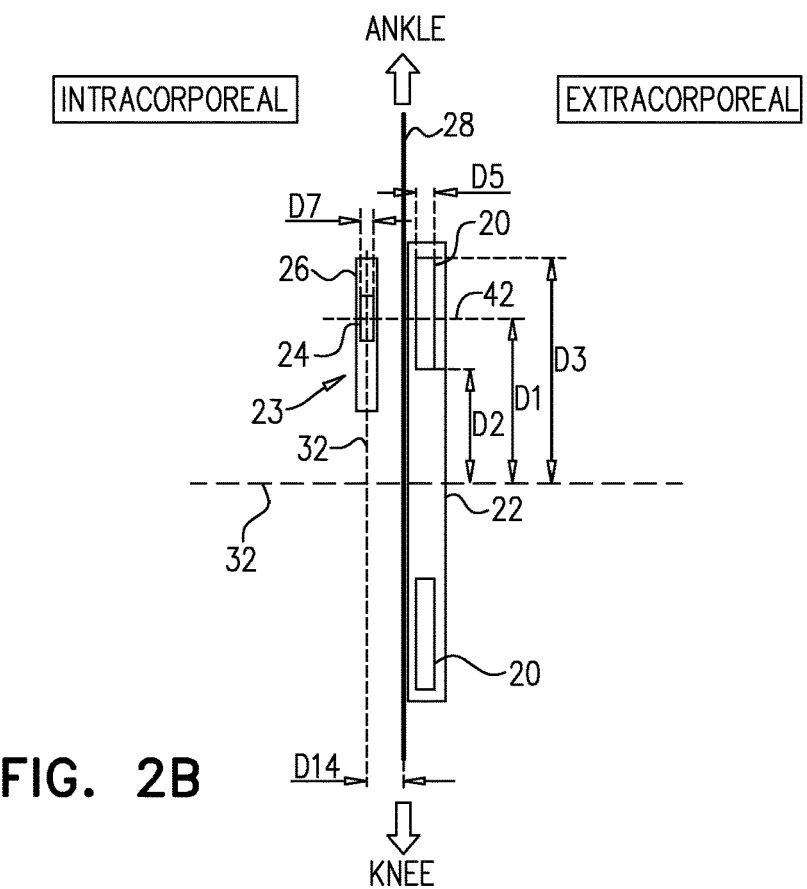

Reference is now made to FIGS. 2A-B, which are schematic illustrations of an orientation of transmitting coil housing 22, and thereby transmitting coil 20, with respect to receiving coil 24, in accordance with some applications of the present invention. For some applications, medical implant 23 is implanted between a knee and an ankle of a subject, closer to the ankle than to the knee, such as is shown in FIGS. 1A-B. Typically, a doctor will implant the medical implant 2-10 cm away from the medial malleolus. Inside medical implant 23, receiving coil 24 is disposed closer to an ankle-side 84 (FIG. 2A) of the medical implant than it is to a knee-side 86 (FIG. 2A) of the medical implant. Space on skin 28 near the ankle however is limited due to the subject's ankle bone and shoe. Efficiency of the power transfer can be improved by ensuring that magnetic fields, e.g., magnetic field 52, generated by the current in transmitting coil 20 are substantially parallel to receiving coil 24 in the vicinity of receiving coil 24. Magnetic fields that are substantially parallel to receiving coil 24, but not in the vicinity of receiving coil 24, e.g., magnetic field 53, do not substantially affect the power transfer.

Therefore, taking into account the limited space available near the ankle, the desired orientation of the generated magnetic fields is accomplished by placing transmitting coil housing 22 against skin 28 such that transmitting coil 20, having a wire disposed at all rotational locations about central longitudinal axis 34, is not centered over receiving coil 24. Rather, only a portion 50 (FIG. 1A) of transmitting coil 20 is disposed over receiving coil 24, such that at one of the rotational locations about central longitudinal axis 34 of transmitting coil 20, a line 38 extending from the wire and substantially parallel to central longitudinal axis 34 of transmitting coil 20 intersects receiving coil 24, and at 180 degrees from the rotational location, a line 40 extending from the wire and substantially parallel to central longitudinal axis 34 of transmitting coil 20 does not intersect receiving coil 24. This orientation of transmitting coil 20, further described hereinbelow, allows for the use of only one transmitting coil 20 to power medical implant 23. Typically, (a) portion 50 of transmitting coil 20, that is disposed over receiving coil 24, is closer to the ankle than (b) a portion 51 of transmitting coil 20, that is not disposed over receiving coil 24, e.g., disposed at 180 degrees from portion 50, is to the ankle (for example as shown in FIG. 1A).

For some applications, medical implant 23 is implanted on a leg between the knee and the ankle, as described hereinabove, in order to treat patients suffering from migraines or cluster headaches using tibial nerve stimulation. Transmitting coil 20 powers medical implant 23 in order to provide neural stimulation to the tibial nerve, for example at a repetition rate of 10-60 Hz. Similarly to over-stimulation of the ulnar nerve for treatment of migraines, over-stimulation of the tibial nerve may cause paresthesia in the active pain centers in the brain, thereby reducing the pain of the migraine or cluster headache.

Figure 3:
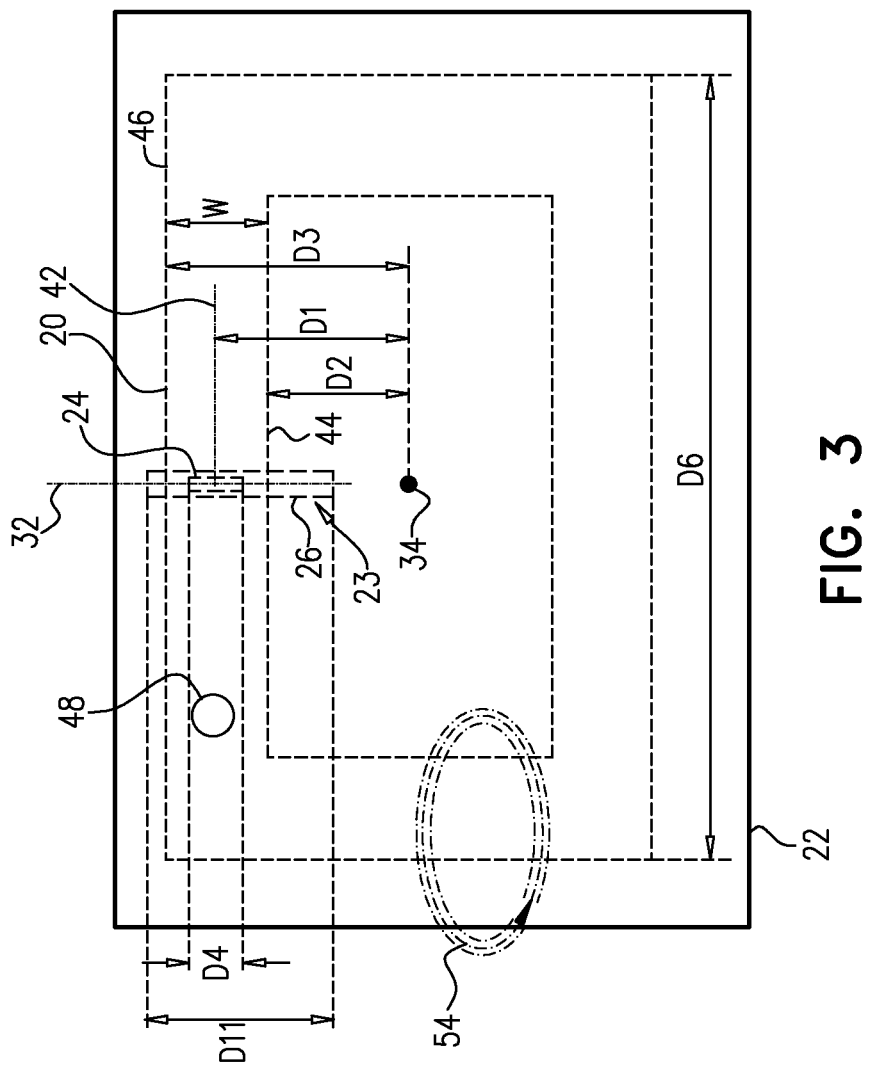
FIG. 3 is a schematic illustration of the orientation of the transmitting coil with respect to the receiving coil, in accordance with some applications of the present invention.

Reference is now made to FIG. 3, which is a schematic illustration of transmitting coil 20 disposed in transmitting coil housing 22 and receiving coil 24 disposed in receiving coil housing 26, in accordance with some applications of the present invention. Typically, transmitting coil housing 22 is placed such that (a) a first distance D1, from central longitudinal axis 34 of transmitting coil 20 to a longitudinal center 42 of receiving coil 24, is 15-45 mm, (b) a second distance D2, from central longitudinal axis 34 of transmitting coil 20 to an inner edge 44 of portion 50 of transmitting coil 20 that is disposed over receiving coil 24, is less than 30 mm, and (c) a third distance D3, from central longitudinal axis 34 of transmitting coil 20 to an outer edge 46 of portion 50 of transmitting coil 20 that is disposed over receiving coil 24, is 40-60 mm. Typically, (a) first distance D1 is greater than second distance D2 and less than third distance D3, and (b) a difference between second distance D2 and third distance D3 is 30-40 mm. The difference between third distance D3 and second distance D2 is referred to hereinbelow as width W of transmitting coil 20.

In order to further improve the efficiency of the power transfer, transmitting coil 20 is typically elongated in a direction perpendicular to central longitudinal axis 32 of receiving coil 24 thus increasing a distance between central longitudinal axis 34 and a wire of transmitting coil 20. Therefore, magnetic fields generated by the current in transmitting coil 20, e.g., magnetic field 54, that are not substantially parallel to receiving coil 24, are farther away from receiving coil 24 thereby they have less of an effect on the induced current in receiving coil 24. For some applications, an average distance D10 (FIG. 4) from the wire of transmitting coil 20 to central longitudinal axis 34 of transmitting coil 20 is less than two times, e.g., 0.6-1.5 times, a square root of a cross-sectional area of a central non-coiled region 56 of transmitting coil 20.

Efficiency of the power transfer is also affected by a depth of implantation of medical implant 23. Typically, medical implant 23 is implanted at a depth D14 (FIG. 2B) of 1-5 cm below skin 28. As used in the present application, including in the claims, the depth of medical implant 23 is the distance from skin 28 to central longitudinal axis 32 of receiving coil 24 measured substantially normal to the skin.

Reference is again made to FIG. 1B. In some applications, an indicator 48 is coupled to transmitting coil housing 22. Control circuitry 36 is configured to activate indicator 48 upon transmitting coil 20 being in an acceptable position with respect to receiving coil 24. For example, indicator 48 may be a visual indicator, an audible indicator, or a vibrator. Typically, indicator 48 is configured to indicate an acceptable position of transmitting coil 20 when the efficiency of the energy transmission between transmitting coil 20 and receiving coil 24 is above a threshold that is at least 85% of the maximum efficiency possible for the patient. For some applications, the maximum efficiency of the power transfer is approximately 5%.

For some applications, control circuitry 36 is able to detect when transmitting coil 20 is in an acceptable position by outputting a signal and subsequently detecting an interference, caused by receiving coil 24, with the signal. Upon detection of the interference, control circuitry 36 activates indicator 48.

Alternatively or additionally, control circuitry 36 is able to ascertain an indication of the efficiency of the energy transmission between transmitting coil 20 and receiving coil 24, and indicator 48 is configured to have a range of indications that are respectively representative of the efficiency ascertained by control circuitry 36. For some applications, the indication of the efficiency is a measurement of power loss in transmitting coil 20. Power loss in transmitting coil 20 may include one or more of the following: (a) power losses that do not appreciably change with the positioning of the transmitting coil, such as losses due to unavoidable resistance of transmitting coil 20 and other losses in the transmitting electronics, and (b) losses in the power transmitted to medical implant 23 which depend on the relative positioning of transmitting coil 20 and receiving coil 24, such as absorption of power in the tissue and surrounding structures. Thus, monitoring the power loss in transmitting coil 20 may facilitate proper positioning of transmitting coil 20 in relation to medical implant 23.

Alternatively or additionally, medical implant 23 is configured to send an output signal to control circuitry 36 upon receiving transmitted power from transmitting coil 20. This output signal may include data indicative of the power received by receiving coil 24 in medical implant 23. Control circuitry 36 receives the data indicative of the power received by receiving coil 24 in medical implant 23, and by comparing it to the power transmitted by transmitting coil 20, determines a parameter indicative of the efficiency of the power transmission. This parameter may be used to indicate to the user: a) if the efficiency is within a range of acceptable values; and b) if repositioning transmitting coil housing 22 has caused an increase or decrease in the power transmission. The indication may be used by a healthcare provider, during an initial training session, to train the patient or family member to correctly position transmitting coil housing 22. Similarly, the indication may be used by the patient or family member each time transmitting coil housing 22 has to be placed on the patient or repositioned. For some applications, the output signal from medical implant 23, indicative of the power received by receiving coil 24, is sent only when needed. For example, the output signal from medical implant 23 may be sent (a) when medical implant 23 is powered-up, (b) during positioning of transmitting coil 20, or (c) when the power received by receiving coil 24 in medical implant 23 is changed unexpectedly, indicating a possible movement of transmitting coil 20 relative to receiving coil 24.

Transmitting coil housing 22 can be positioned on skin 28 by placing housing 22 against skin 28 and subsequently sliding transmitting coil housing 22 along skin 28 until indicator 48 indicates that transmitting coil 20 is in an acceptable position with respect to receiving coil 24. In some applications, control circuitry 36 is further configured to activate indicator 48 again upon transmitting coil 20 no longer being in an acceptable position with respect to receiving coil 24.

Figure 4:
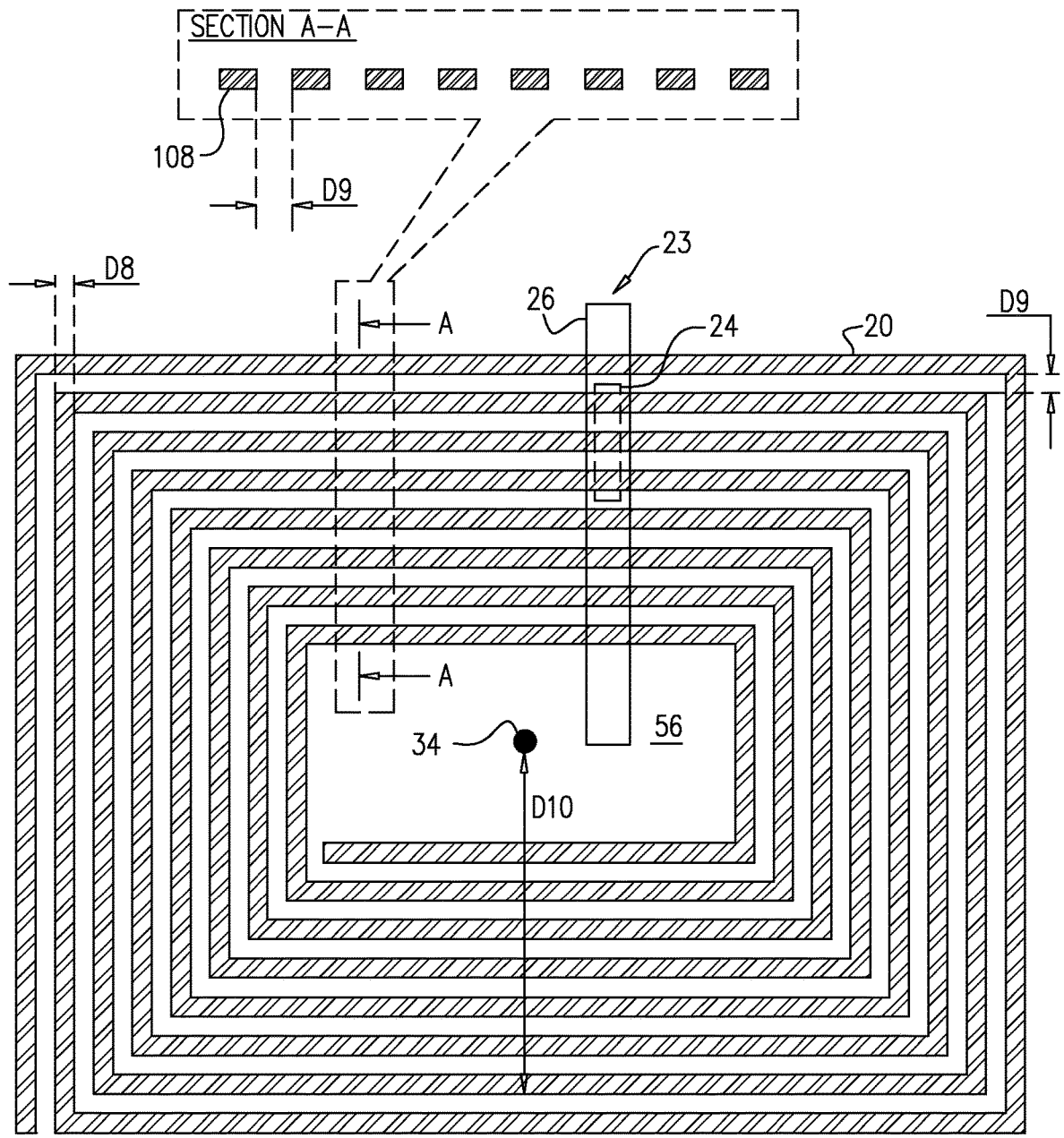
FIG. 4 is a schematic illustration of a top view and a cross-section of the transmitting coil, in accordance with some applications of the present invention.

Reference is now made to FIG. 4, which is a schematic illustration of transmitting coil 20 in accordance with some applications of the present invention. Typically, transmitting coil 20 is a planar coil having between 4 and 10 turns, e.g., 8 turns. A line spacing D9 of adjacent coplanar wires in transmitting coil 20 is typically 0.25-3 mm, e.g., 2 mm, and a line width D8 of the wires in transmitting coil 20 is typically 1-4 mm, e.g., 2 mm. For some applications, transmitting coil 20 comprises a plurality of planar layers, e.g., two planar layers.

One or more dimensions of transmitting coil 20 that highlight the planar properties of transmitting coil 20 are as follows:
- a height D5 (FIG. 2B) of transmitting coil 20, measured along central longitudinal axis 34 of transmitting coil 20 when transmitting coil 20 is laid flat, i.e. the thickness of transmitting coil 20, is at least 300 and/or less than 600 microns;
- an outer diameter D6 (FIG. 3) of transmitting coil 20 is at least 100 mm and/or less than 140 mm;
- a ratio of outer diameter D6 of transmitting coil 20 to height D5 of transmitting coil 20 is at least 150.

As used in the present application, including in the claims, outer diameter D6 of transmitting coil 20 is the largest dimension of transmitting coil 20 from one side of the coil to the other, measured perpendicular to central longitudinal axis 34 of transmitting coil 20.

Typically, a cross-sectional area 108 of the wire of transmitting coil 20 is rectangular when the cross-section, e.g., cross-section A-A shown in FIG. 4, is taken perpendicular to a direction of current flow within the wire.

Typically, receiving coil 24 is a cylindrical coil having 10-40 turns, e.g., 20 turns, and comprising a ferrite core. For some applications, one or more dimensions of receiving coil 24 are as follows:

- a longitudinal length D4 (FIG. 3) of receiving coil 24 is at least 3 mm and/or less than 15 mm;
- an outer diameter D7 of receiving coil 24 (FIG. 2B) is at least 0.6 mm and/or less than 1.5 mm; and/or
- a ratio of outer diameter D7 of receiving coil 24 to longitudinal length D4 of receiving coil 24 is less than 0.5.

Typically, receiving coil housing 26 is longitudinally longer than receiving coil 24, to accommodate for control circuitry disposed within medical implant 23. For some applications, a longitudinal length D11 of receiving coil housing 26 is at least 30 mm and/or less than 45 mm. Medical implant 23 may also comprise a plurality of electrodes.

For some applications, some dimensional relationships between transmitting coil 20 and receiving coil 24 are expressed according to a set of one or more of the following options:
- (a) a first ratio, of outer diameter D6 (FIG. 3) of transmitting coil 20 to height D5 (FIG. 2B) of transmitting coil 20 is at least 150, (b) a second ratio, of outer diameter D7 (FIG. 2B) of receiving coil 24 to longitudinal length D4 (FIG. 3) of receiving coil 24 is less than 0.5, and (c) a ratio of the first ratio to the second ratio is at least 300;
- a ratio of width W of transmitting coil 20 to longitudinal length D4 (FIG. 3) of receiving coil 24 is greater than 0.5;
- a ratio of width W of transmitting coil 20 to longitudinal length D4 of receiving coil 24 is less than 1.5; and/or
- a ratio of width W of transmitting coil 20 to longitudinal length D4 of receiving coil 24 is at least 0.5 and/or less than 1.5.

Figure 5B:
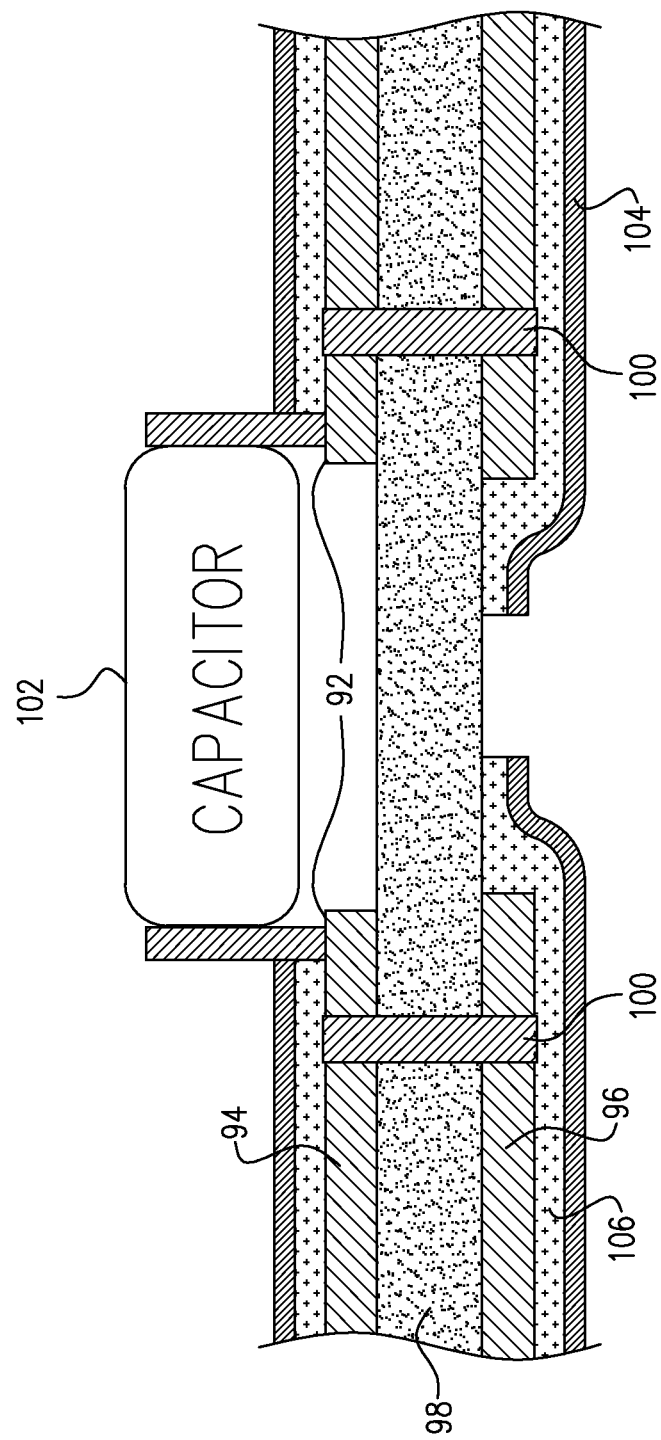

Reference is now made to FIGS. 5A-B, which are schematic illustrations of transmitting coil 20, in accordance with some applications of the present invention. FIG. 5A depicts schematic cross-sectional views of several locations of transmitting coil 20, in accordance with some applications of the present invention. For some applications, transmitting coil 20 comprises two planar layers 94 and 96 disposed on either side of a flexible printed circuit board (PCB) 98. A height D12 of each planar layer 94 and 96, measured along longitudinal axis 34 of transmitting coil 20, is 15-100 microns, e.g., 35 or 70 microns, and a thickness D13 of flexible PCB 98 is 100-200 microns, e.g., 150 microns. For some applications, at least once along each turn of transmitting coil 20 the two planar layers 94 and 96 are conductively connected to each other, such that current may flow from one layer to the other. For example, a via 100 filled with solder may be used to conductively connect the two planar layers 94 and 96.

Additionally, a capacitor 102 is coupled to transmitting coil 20 at at least one location along at least one turn of transmitting coil 20. Typically, capacitor 102 is attached to an exposed pad 92 of one of planar layers 94 or 96. For some applications, as seen in FIG. 5A, capacitor 102 is electrically coupled to both planar layers 94 and 96 by being coupled to two or more vias 100 in pad 92. For some applications, as seen in FIG. 5B, capacitor 102 is directly soldered to pad 92. For some applications, a plurality of capacitors 102 are coupled to transmitting coil 20 such that at least one capacitor 102 is coupled to transmitting coil 20 at at least one location along each turn of transmitting coil 20.

Typically, an insulating cover 104 is coupled, e.g., glued, to both planar layers 94 and 96 of transmitting coil 20 on flexible PCB 98. For some applications, a thickness D17 of a layer of glue 106 between cover 104 and each planar layer 94 and 96 is 15-50 microns. For some applications, a thickness D18 of cover 104 is 15-100 microns.

FIG. 5A shows both a cross-section and a top-view of transmitting coil 20. In the top-view, one planar layer 94 can be seen on flexible PCB 98, with one capacitor 102 coupled to each turn of transmitting coil 20. A plurality of solder-filled vias 100 are coupled to each turn of transmitting coil 20 to conductively connect planar layer 94 to planar layer 96, which is coupled to the other side of flexible PCB 98 and not visible in this figure. For some applications, vias 100 are positioned at the corners of each turn of transmitting coil 20, and on either side of each capacitor 102, as shown in FIG. 5A. Alternatively or additionally a plurality of vias 100, e.g., 2-30 vias 100 may be positioned anywhere along each turn of transmitting coil 20.

Figure 6:
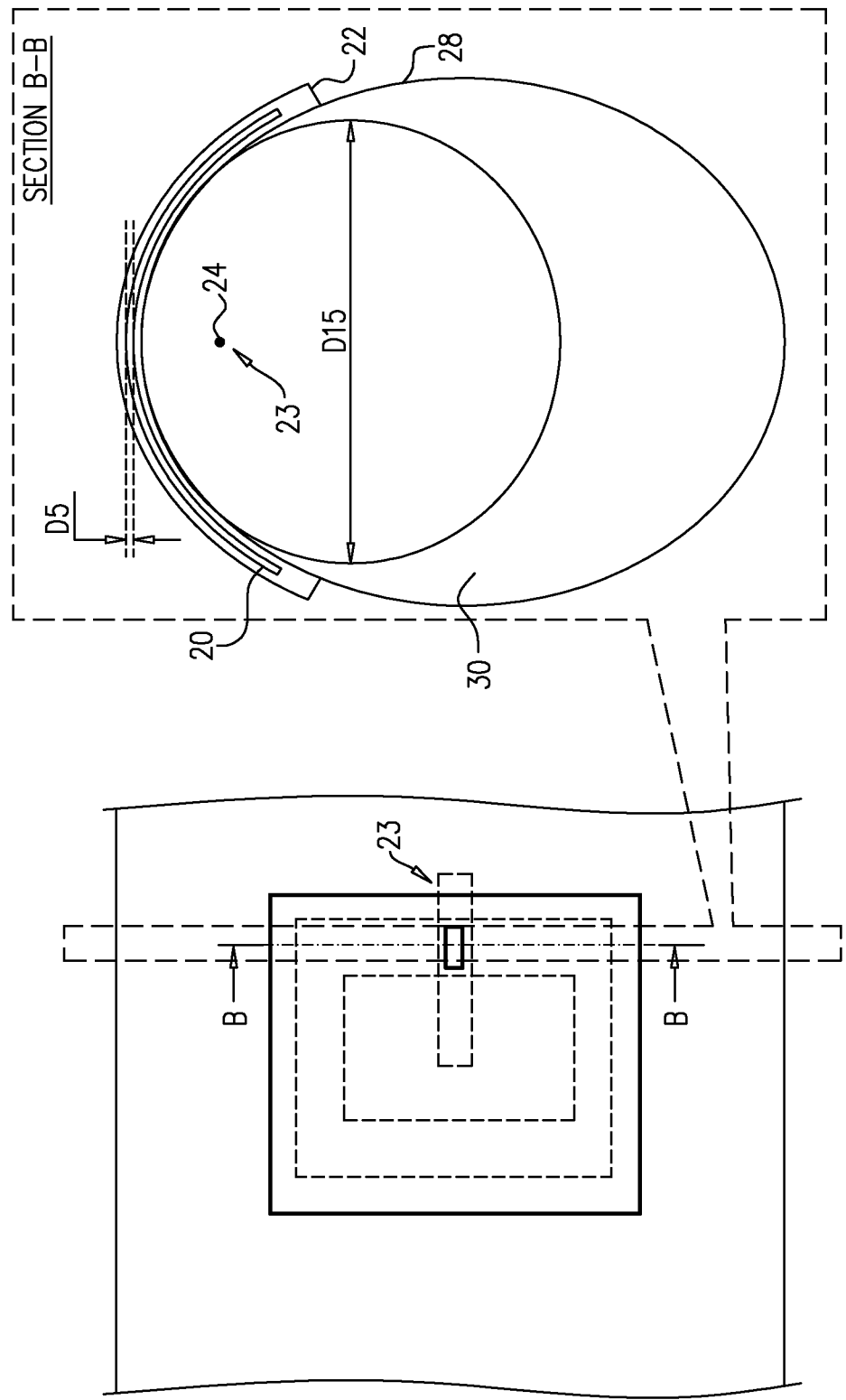
FIGS. 6-7 are schematic illustrations of the transmitting coil in the housing being flexed to conform to a curve of a limb of the subject, in accordance with some applications of the present invention.
Figure 7:
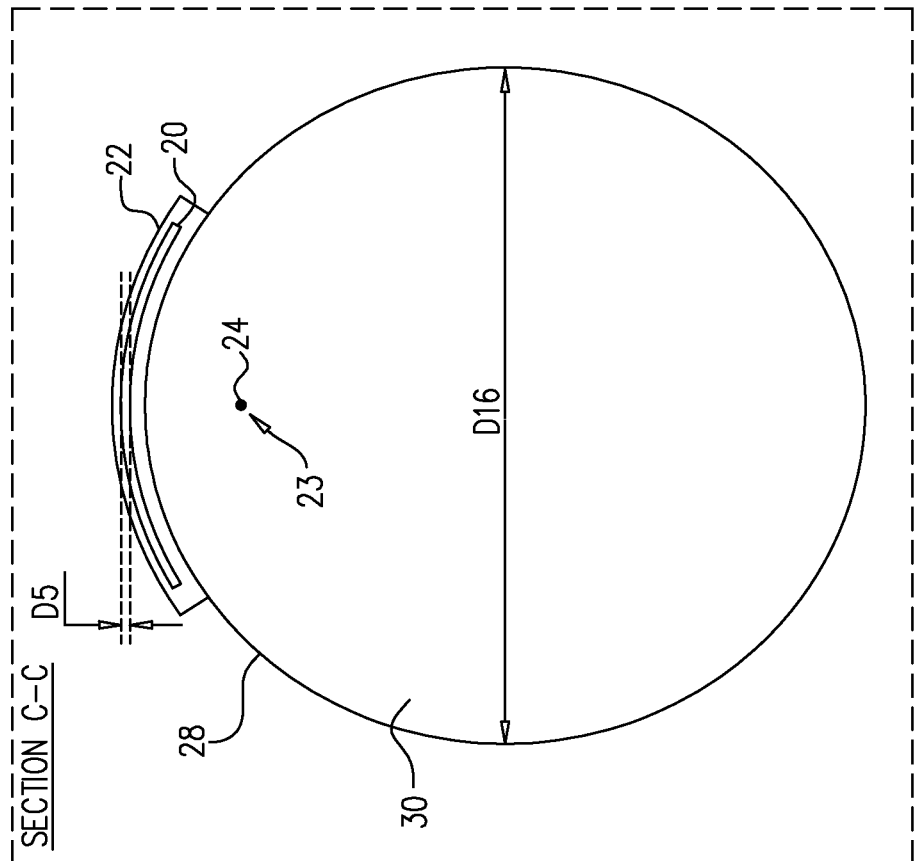
Figure 7:
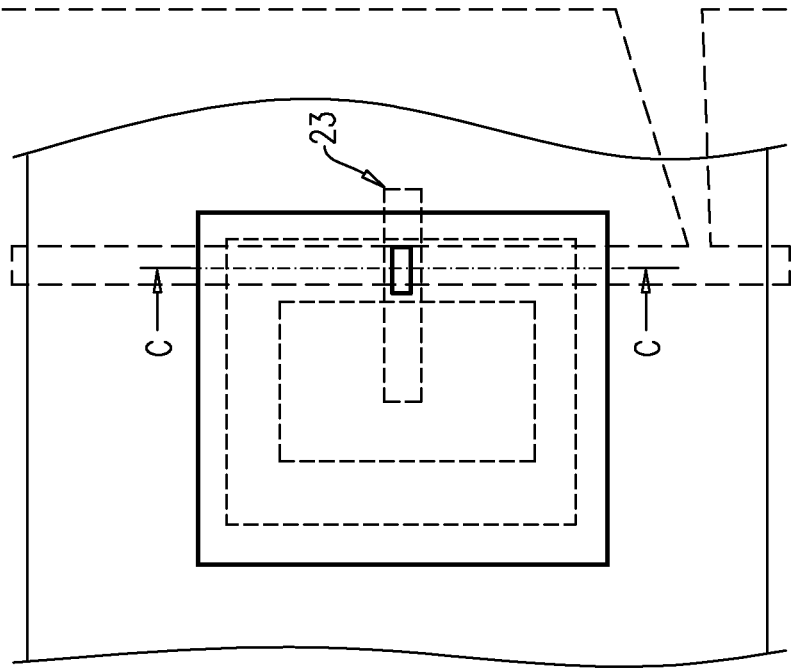
Figure 8:
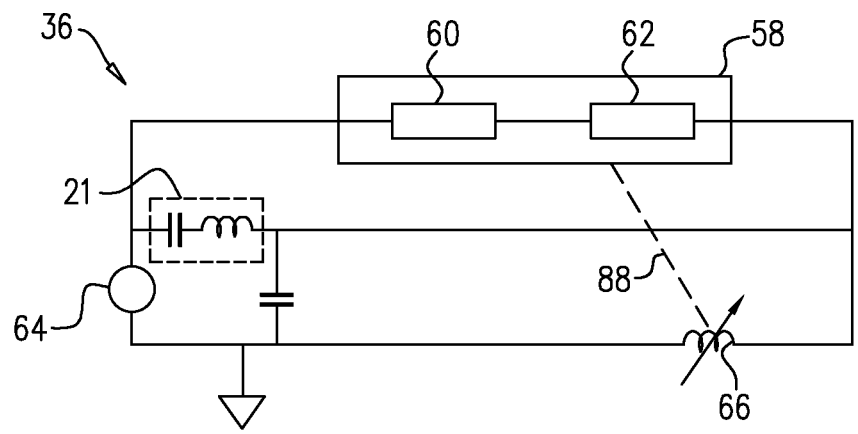
FIGS. 8-13 are schematic illustrations of control circuitry of the transmitting coil, in accordance with some applications of the present invention.
Figure 9:
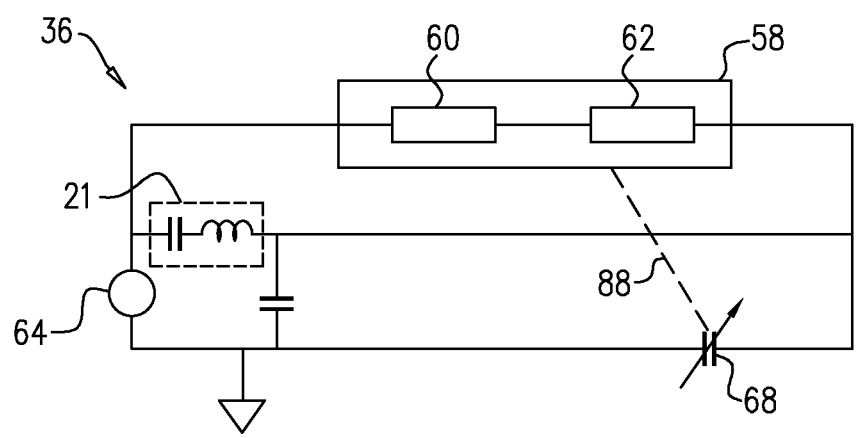
Figure 10:
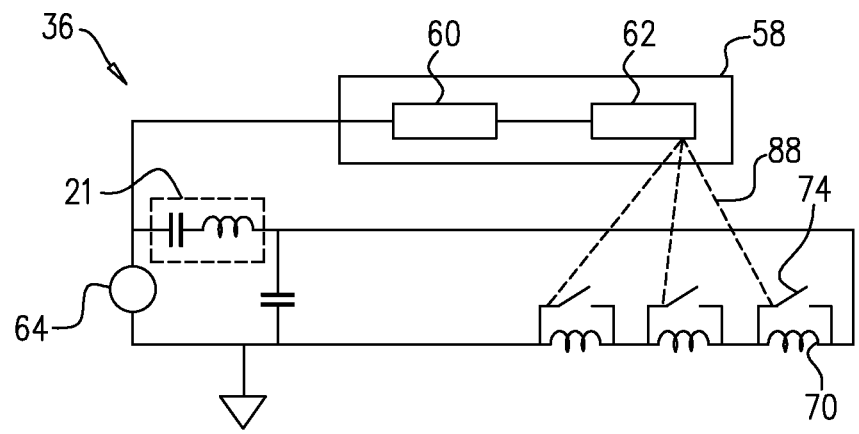
Figure 11:
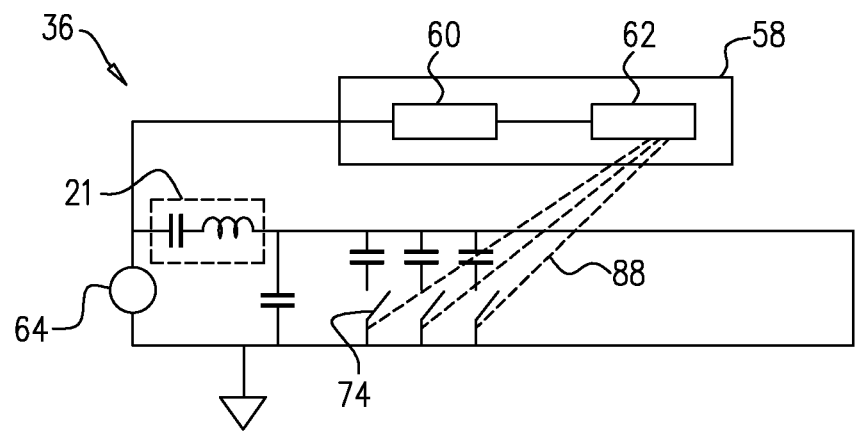

Reference is now made to FIGS. 6-7, which are schematic illustrations of transmitting coil housing 22, comprising transmitting coil 20, placed against skin 28 of limb 30 of the subject, in accordance with some applications of the present invention. Typically, in order to allow comfortable placement of transmitting housing 22 against limb 30, transmitting coil housing 22 and transmitting coil 20 are configured to be flexible such that they can substantially conform to a lateral wall of cylinders having diameters that range between a diameter D15 (FIG. 6) of 8 cm, e.g., a wrist, and a diameter D16 (FIG. 7) of 50 cm, e.g., a torso or obese upper leg. The flexing of transmitting coil 20, however, may cause the resonance frequency of transmitting coil 20 to fluctuate rather than remain at a nominal resonance frequency that occurs in the absence of any forces applied to transmitting coil 20 and is near the frequency of the current output by control circuitry 36.

Reference is now made to FIGS. 8-13, which are circuit diagrams of control circuitry 36, in accordance with some applications of the present invention. Portion 21 of control circuitry 36, as shown in FIGS. 8-13, is a model of transmitting coil 20 as shown in FIGS. 1-7. For some applications, a sensor 58 is coupled to control circuitry 36. Sensor 58 is coupled to control circuitry 36 and is configured to (a) determine an extent of divergence of (i) the resonance frequency of transmitting coil when transmitting coil 20 is flexed from (ii) the nominal resonance frequency of transmitting coil 20, and (b) subsequently output a signal to one or more electrical components that are coupled to control circuitry 36 and configured to tune the resonance frequency of transmitting coil 20 in response to the determination of sensor 58.

For some applications, sensor 58 comprises a phase detector 60 and a feedback calculator 62 (for example, as shown in FIGS. 8-12). Phase detector 60 is configured to (a) determine a phase difference between the phase of the current output by signal generator 64 and the phase of either a current or a voltage on at least one component of transmitting coil 20, and (b) output a signal to feedback calculator 62 according to the determination. After receiving the signal from phase detector 60, feedback calculator 62 (a) determines a necessary change in the resonance frequency of transmitting coil 20 that will reduce the extent of divergence of (i) the resonance frequency of transmitting coil 20 when transmitting coil 20 is flexed from (ii) the nominal resonance frequency of transmitting coil 20 and (b) outputs a signal to the electrical components according to the determination. Dashed lines 88 (FIGS. 8-12 represent feedback calculator 62 controlling each respective switch 74.

Figure 13:
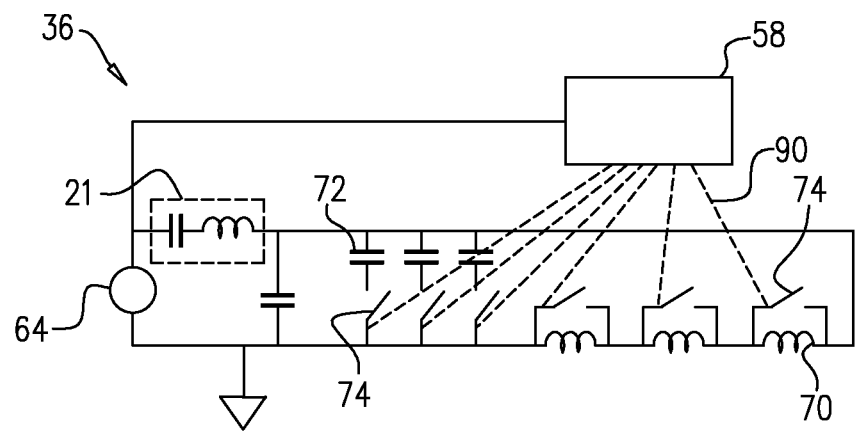

For some applications (e.g., as shown in FIG. 13), sensor 58 does not comprise phase detector 60 and feedback calculator 62. Rather, sensor 58 is configured to (a) measure a parameter that is indicative of both the frequency output by signal generator 64 and the resonance frequency of transmitting coil 20, e.g., by measuring the power output of transmitting coil 20, (b) look up at least one value in a look-up table with respect to the measured parameter, and (c) output a signal to the electrical components based on the looked-up value. Dashed line 90 (FIG. 13) represents sensor 58 controlling each respective switch 74.

For some applications, at least one of the electrical components is a variable inductor 66 (FIG. 8), whose inductance is varied according to the signal output by sensor 58. Variation of the inductance of variable inductor 66, in turn, cause variations in the resonance frequency of transmitting coil 20.

For some applications, at least one of the electrical components is a variable capacitor 68 (FIG. 9), whose capacitance is varied according to the signal output by sensor 58. Variation of the capacitance of variable capacitor 68, in turn, cause variations in the resonance frequency of transmitting coil 20.

Figure 12:
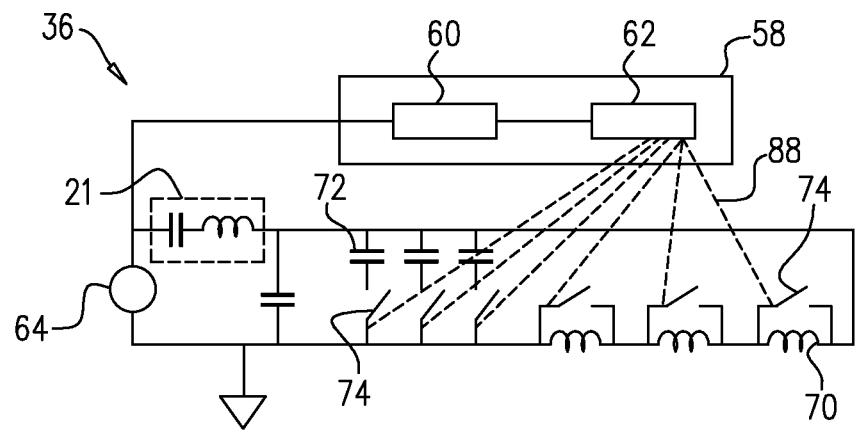

For some applications, the one or more electrical components is a (a) a plurality of inductors 70, e.g., 3-9 inductors 70, coupled in series (FIG. 10), (b) a plurality of capacitors 72, e.g., 4-10 capacitors 72, coupled in parallel (FIG. 11), or (c) a combination of inductors 70, coupled in series, and capacitors 72, coupled in parallel (FIG. 12). When a plurality of inductors are used, typically a first one of inductors 70 has an inductance of 1.5-2.5 times, e.g., 2 times, an inductance of another one of inductors 70, and/or each one of at least half of inductors 70 has an inductance that is twice an inductance of another one of inductors 70. For example, 9 inductors 70 may have respective inductances of 2, 4, 8, 16, 32, 64, 128, 256, and 512 (arbitrary units). Similar sequencing may be used for a plurality of capacitors 72. For example, 10 capacitors 72 may have respective capacitances of 2, 4, 8, 16, 32, 64, 128, 256, 512, and 1024 (arbitrary units).

Typically, control circuitry 36 tunes the resonance frequency of transmitting coil 20, according to the signal output by sensor 58, by activating and/or deactivating at least one of a plurality of switches 74, each switch 74 being coupled to a respective one of the electrical components, in order to facilitate or inhibit current flow through the respective electrical component. In order to easily be able to increase and decrease the resonance frequency of transmitting coil 20, as necessary according to the signal output by sensor 58, control circuitry 36 is configured such that, when the extent of divergence of (a) the resonance frequency of transmitting coil 20 when transmitting coil 20 is flexed from (b) the nominal resonance frequency of transmitting coil 20 is reduced, at least one of switches 74 is activated, allowing current to flow through a respective electrical component, and at least another switch 74 is deactivated, inhibiting current from flowing through another respective electrical component. For some applications, control circuitry 36 is configured to dither the resonance frequency of transmitting coil 20 by repeatedly activating and deactivating at least one of switches 74 to alternatingly facilitate and inhibit current flow through a respective electrical component.

For some applications, a wider range of variation of the resonance frequency of transmitting coil 20 may be achieved by having at least one electrical component (a) configured to vary the resonance frequency of transmitting coil 20 by more than the remaining electrical components are configured to vary the resonance frequency of transmitting coil 20 and (b) coupled to a manually-operated switch. The manually-operated switch may be activated and/or deactivated by a user to provide gross tuning of the resonance frequency of transmitting coil 20 and the remaining switches 74 activated and/or deactivated by control circuitry 36 to provide fine tuning of the resonance frequency of transmitting coil 20.

Figure 14:
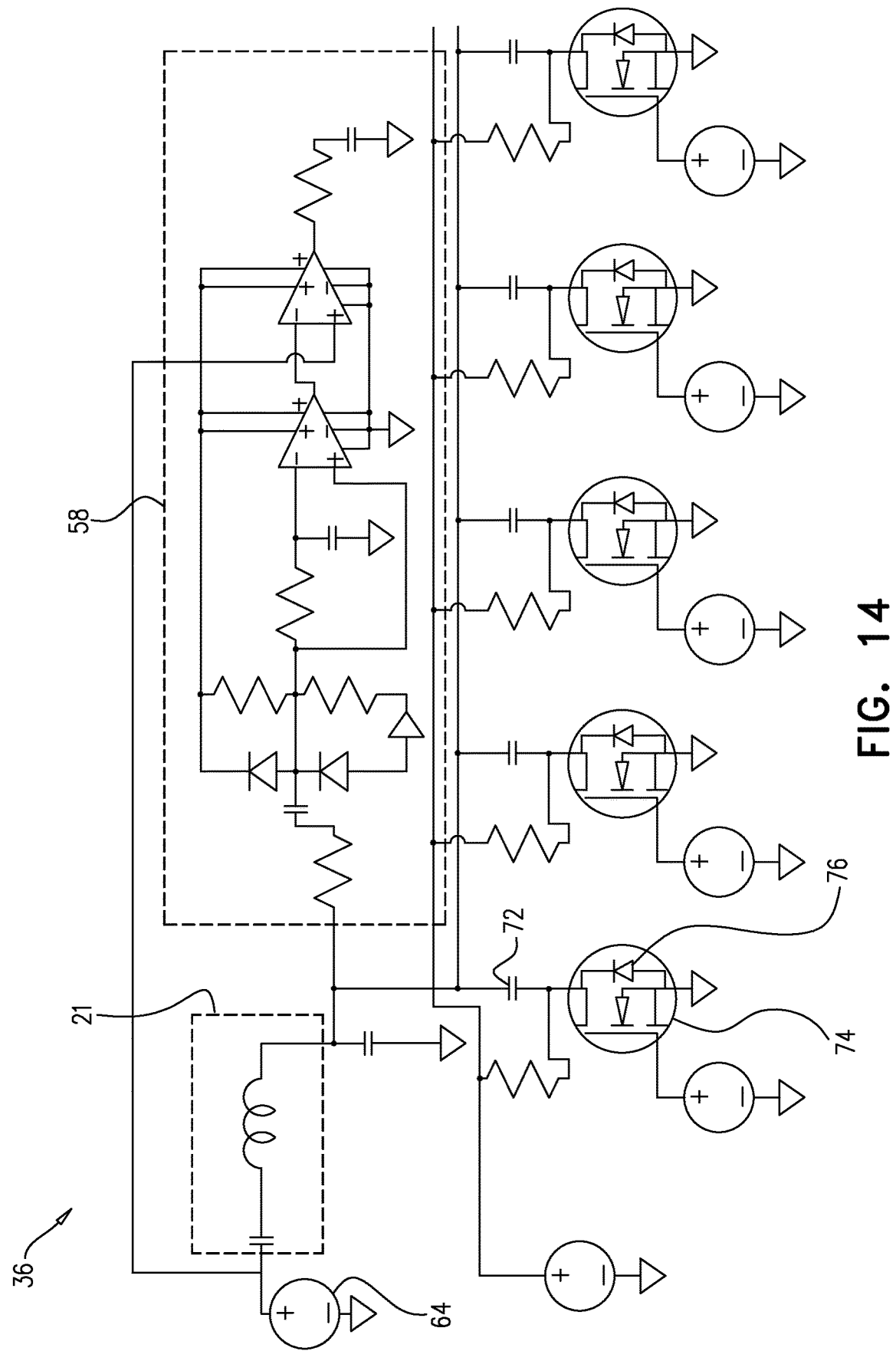
FIG. 14 is a circuit diagram of the control circuitry of the transmitting coil, in accordance with some applications of the present invention.

Reference is now made to FIG. 14, which is a circuit diagram of control circuitry 36, in accordance with some applications of the present invention. For some applications, switches 74 comprise transistors 76 (e.g., field effect transistors, e.g., MOSFETs, as shown in FIG. 14) that behave, in their off state, as either diodes or variable capacitors, such that each switch 74 has a respective parasitic capacitance that depends on a respective voltage applied to each switch 74.

Figure 15:
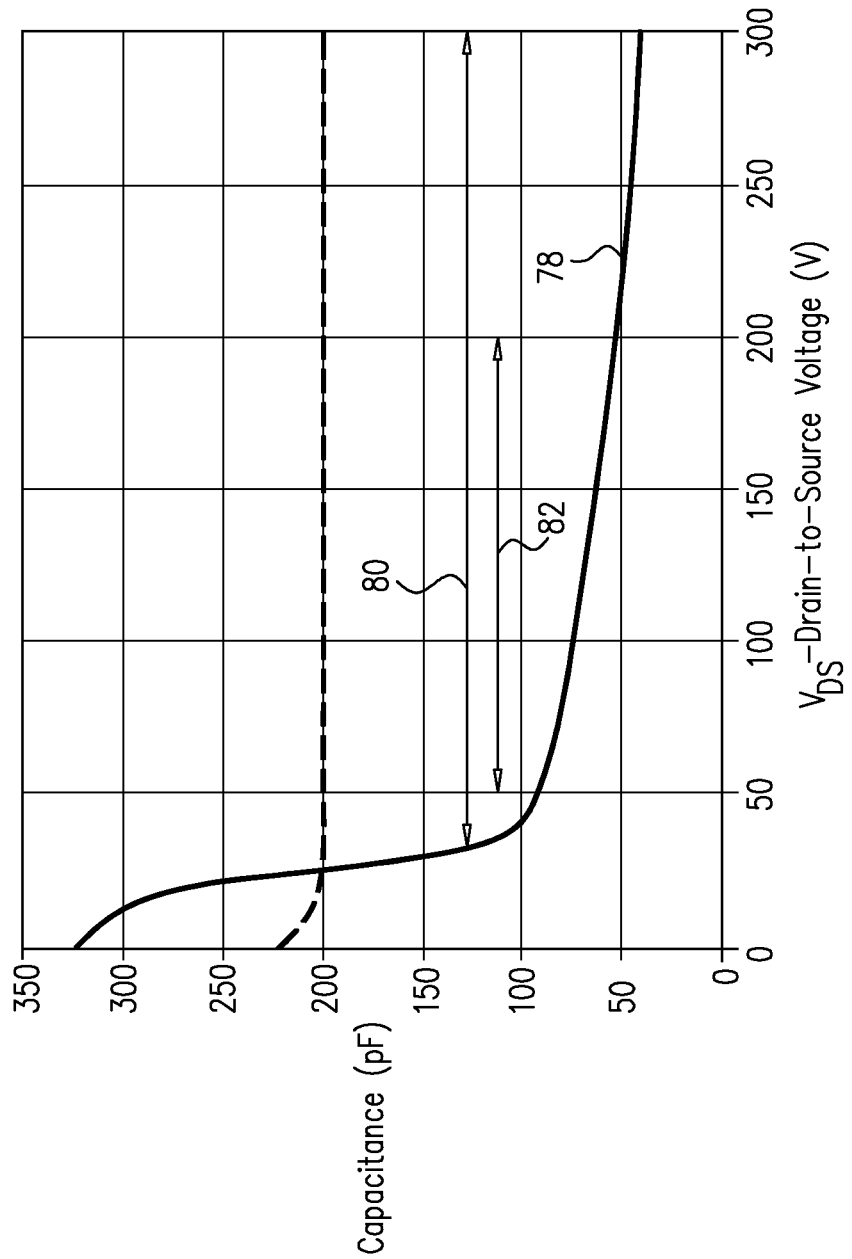
FIG. 15 is a graph showing rate of change of capacitance versus drain-to-source voltage change of a switch coupled to the control circuitry, in accordance with some applications of the present invention.

Reference is now made to FIG. 15, which is a graph showing rate of capacitance change versus drain-to-source voltage change of a switch, such as a switch 74 in control circuitry 36, in accordance with some applications of the present invention. Curve 78 of the graph shows (a) how the rate of capacitance change of a switch, such as switch 74, is significantly decreased when the switch is activated by an alternating current (AC) or, as shown in FIG. 14, a DC voltage, of over 50 volts, and (b) how the output capacitance of a switch, such as switch 74, significantly decreases as the drain-to-source voltage is increased from 0-50 volts. As shown by arrows 80 and 82, in order to reduce an effect that the respective parasitic capacitances of respective switches 74 may have on the resonance frequency of transmitting coil 20, control circuitry 36 is configured to activate switches 74 by applying a respective AC or, as shown in FIG. 14, DC voltage of 30-300 volts (arrow 80), e.g., 50-200 volts (arrow 82), to each switch 74, thereby reducing the output capacitance of each switch 74, as well as reducing the variation in output capacitance of each switch 74 over the duration of the AC voltage cycle or over the duration of the application of the DC voltage.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a medical implant that comprises a receiving coil, the apparatus comprising:
    a flexible housing configured to be placed against skin of a subject;
    a flexible transmitting coil disposed in the housing;
    control circuitry configured to transmit power to the medical implant by driving a current through the transmitting coil that induces an induced current in the receiving coil;
    a sensor coupled to the control circuitry, the sensor configured to determine an extent of divergence of (a) a resonance frequency of the transmitting coil when the transmitting coil is flexed from (b) a nominal resonance frequency of the transmitting coil, occurring in the absence of any forces applied to the transmitting coil, and configured to output a signal according to the determination;
    one or more electrical components, coupled to the control circuitry and configured to tune the resonance frequency of the transmitting coil in response to the determination of the sensor; and
    a plurality of switches, each switch coupled to a respective one of the electrical components,
        the control circuitry being configured to apply a respective DC voltage to each switch, and
        the switches comprising transistors having respective capacitances that are dependent on the respective DC voltage applied to each switch.

2. The apparatus according to claim 1, wherein the control circuitry is configured to set the frequency of the current output by the control circuitry to be between 1 and 20 MHz.

3. The apparatus according to claim 1, wherein the flexible transmitting coil is configured to flex such that it can substantially conform to a lateral wall of a cylinder having a diameter between 8 and 50 cm.

4. The apparatus according to claim 1, wherein the sensor comprises a phase detector, configured to (a) determine a phase difference between the phase of the current output by the control circuitry, and the phase of either a current or a voltage on at least one component of the transmitting coil, wherein the phase difference is due to flexing of the transmitting coil, and (b) output a signal according to the determination.

5. The apparatus according to claim 4, wherein the control circuitry comprises a feedback calculator configured to:
    (a) receive the signal output by the phase detector,
    (b) determine, according to the signal output by the phase detector, a necessary change in the resonance frequency of the transmitting coil, in order to reduce the extent of divergence of (a) the resonance frequency of the transmitting coil when the transmitting coil is flexed from (b) the nominal resonance frequency of the transmitting coil, and
    (c) output a signal to the one or more electrical components, according to the determination.

6. The apparatus according to claim 1, wherein the sensor is configured to:
    (a) measure a parameter that is indicative of the frequency of the current output by the control circuitry and the resonance frequency of the transmitting coil,
    (b) look up at least one value in a look-up table with respect to the measured parameter, and
    (c) output a signal to the one or more electrical components based on the looked-up value.

7. The apparatus according to claim 6, wherein the control circuitry is configured such that the measured parameter is a level of power output by the transmitting coil.

8. The apparatus according to claim 1, wherein the control circuitry is configured to tune the resonance frequency of the transmitting coil, according to the signal output by the sensor, by activating at least one of the plurality of switches to facilitate or inhibit current flow through the respective electrical component.

9. The apparatus according to claim 1, wherein at least one of the plurality of switches is configured to be manually operated and the remaining switches are configured to be operated by the control circuitry, wherein (a) the electrical component coupled to the manually-operated switch is configured to vary the resonance frequency of the transmitting coil by more than (b) the electrical components coupled to the switches operated by the control circuitry are configured to vary the resonance frequency of the transmitting coil.

10. A system, comprising the apparatus according to claim 1, the system further comprising the medical implant.

* * * * *